United States Patent
Ionidis

(10) Patent No.: US 11,020,328 B2
(45) Date of Patent: Jun. 1, 2021

(54) COSMETIC WATER-IN-OIL MICROEMULSION

(71) Applicant: IONIA AZURÉ AG, Zürich (CH)

(72) Inventor: Georgios Ionidis, Zürich (CH)

(73) Assignee: IONIA AZURÉ AG, Zürich (CH)

( * ) Notice: Subject to any disclaimer, the term of this patent is extended or adjusted under 35 U.S.C. 154(b) by 0 days.

(21) Appl. No.: 16/332,162

(22) PCT Filed: Oct. 5, 2017

(86) PCT No.: PCT/EP2017/001173
§ 371 (c)(1),
(2) Date: Mar. 11, 2019

(87) PCT Pub. No.: WO2018/068884
PCT Pub. Date: Apr. 19, 2018

(65) Prior Publication Data
US 2019/0224085 A1    Jul. 25, 2019

(30) Foreign Application Priority Data
Oct. 11, 2016  (EP) .................................... 16002186

(51) Int. Cl.
*A61K 8/06*  (2006.01)
*A61K 8/31*  (2006.01)
(Continued)

(52) U.S. Cl.
CPC .............. *A61K 8/068* (2013.01); *A61K 8/064* (2013.01); *A61K 8/31* (2013.01); *A61K 8/342* (2013.01);
(Continued)

(58) Field of Classification Search
None
See application file for complete search history.

(56) References Cited

U.S. PATENT DOCUMENTS

| 4,797,273 A | * | 1/1989 | Linn ...................... A61K 8/068 424/59 |
| 6,936,265 B2 | * | 8/2005 | Bleckmann ............ A61Q 19/00 424/401 |

(Continued)

FOREIGN PATENT DOCUMENTS

EP     1 639 989 A1    3/2006

OTHER PUBLICATIONS

BASF Emollients (http://www.eurotradingonline.it/wp-content/uploads/2014/12/Emollient-spreadsheet-.pdf, Jan. 1, 2015) (Year: 2015).*

(Continued)

*Primary Examiner* — Celeste A Roney
(74) *Attorney, Agent, or Firm* — Birch, Stewart, Kolasch & Birch, LLP

(57) ABSTRACT

A cosmetic water-in-oil microemulsion having advantageous rheological properties comprising: i) 20-40% w/w of oil phase ingredients with spreadability value of above 1700 mm2/10 min, ii) 15-35% w/w of oil phase ingredients with spreadability value between 1000 and 1700 mm2/10 min, iii) 1-15% w/w of oil phase ingredients with spreadability value between 500 and 999 mm2/10 min, iv) 0-10% w/w of oil phase ingredients with spreadability value of below 500 mm2/10 min, v) 5-30% w/w of fatty acid ester(s) of glycerol or fatty acid ester(s) of polyglycerol, vi) 5-20% w/w of water, co-surfactant(s) and optionally co-solvent(s), cosmetic active ingredient(s), skin care ingredient(s), water-soluble extract(s) of plant material and cosmetic auxiliary ingredient(s).

20 Claims, 1 Drawing Sheet

(51) Int. Cl.
*A61K 8/34* (2006.01)
*A61K 8/37* (2006.01)
*A61K 8/39* (2006.01)
*A61Q 19/00* (2006.01)
*A61K 8/92* (2006.01)

(52) U.S. Cl.
CPC ............... *A61K 8/345* (2013.01); *A61K 8/37* (2013.01); *A61K 8/39* (2013.01); *A61K 8/922* (2013.01); *A61Q 19/00* (2013.01)

(56) References Cited

U.S. PATENT DOCUMENTS

| | | | |
|---|---|---|---|
| 2006/0078525 A1* | 4/2006 | Tomokuni | A61K 8/068 424/70.13 |
| 2006/0193810 A1 | 8/2006 | Mori | |
| 2011/0177019 A1 | 7/2011 | Dickinson et al. | |
| 2015/0038592 A1* | 2/2015 | Von Der Fecht | A61K 8/732 514/738 |

OTHER PUBLICATIONS

Dr. Straetmans Chemical Products (http://www.bisi.cz/cmsres.axd/get/cms$7CVwRhc3USVqgzxkKF96gl $2BE0hVa9TBhlwwHdpDedLKRb8cBSs7zS997r0Z$2BLQ3Mw38uPTZd6LSvCiw9TLFgEAWV2TDP$2FuM6TwutuWVNnje1s$3D, Apr. 11, 2008) (Year: 2008).*
Natural Organic Skincare (https://www.naturalorganicskincare.com/edelweiss-extract, /Jul. 29, 2014). (Year: 2014).*

* cited by examiner

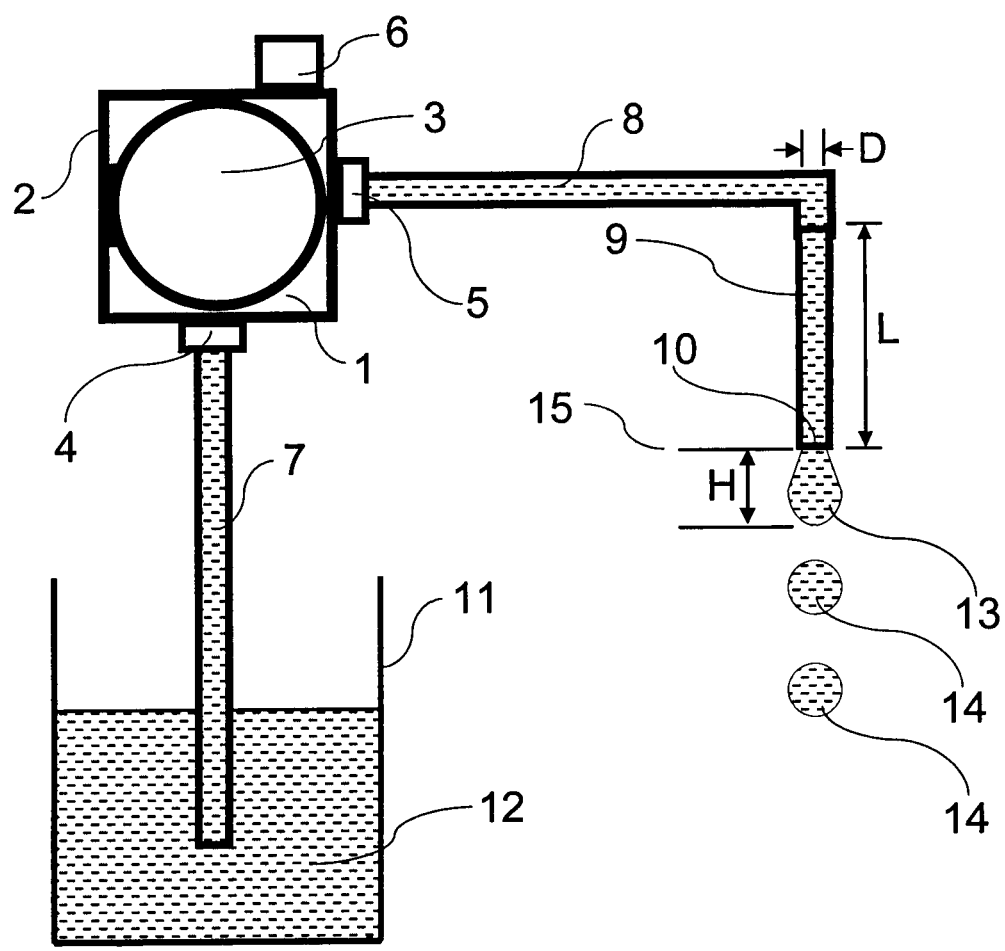

COSMETIC WATER-IN-OIL MICROEMULSION

The present invention relates to a cosmetic water-in-oil microemulsion with advantageous rheological properties compared to the conventional cosmetic water-in-oil microemulsions. Skin care is the complex of measures to keep the skin appearance in healthy and pleasant state. Cosmetic preparations for skin care usually contain both oily or oil soluble ingredients and water or water soluble ingredients and often exist as emulsions. An emulsion is a mixture of two or more liquids that are non-miscible or limitedly miscible, whereas one liquid (referred to as the dispersed phase or the discontinuous phase) is dispersed as small globules in the other (the continuous phase). In preparations for skin care, one phase consists usually of water or water containing water-soluble substances and is referred to as the aqueous phase and the second phase usually consists of water-insoluble oils, emollients, waxes or similar ingredients and is referred to as the oil phase. When oil globules are dispersed in continuous aqueous phase, the emulsion is referred to as oil-in-water or O/W emulsion. When water globules are dispersed in continuous oil phase, the emulsion is referred to as water-in-oil W/O emulsion. Multiphase types of emulsions, such as O/W/O or W/O/W also exist. An emulsion is non-transparent, appearing mostly white, because light gets scattered at the dispersed phase globules. The continuous phase will generally be the one that most influences the sensory and physicochemical properties of the emulsion.

Merely dispersing the dispersed phase in the continuous phase usually creates unstable emulsions, because the dispersed globules quickly coalesce and re-form a separate liquid layer. Adding an emulsifier stabilizes the emulsion. In absence of emulsifier, the relatively high surface tension (interfacial energy per unit area) of the oil and aqueous phases will tend to minimize the surface area of the fluid phases, with the result that at rest the phases will be in touch at the smallest surface possible, effectively creating two strata, one of aqueous phase and one of oil phase. The emulsifier decreases the surface tension between the oil and aqueous phases and enables the creation of stable dispersed phase globules. An emulsifier is an amphiphilic substance having a polar and apolar (non-polar) parts, with polar parts preferentially interacting with aqueous phase and non-polar parts preferentially interacting with the oil phase. The emulsifier thus positions itself at the aqueous/oil interphase. When sufficient amount of emulsifier is present, the dispersed phase globules are surrounded by it forming the so called micelles, which then can be stably dispersed in the continuous phase. The emulsifier also keeps the dispersed phase globules apart, for example by sterically preventing globule contact. The emulsion stabilized by an emulsifier is usually stable for the length of time acceptable for a consumer product, for example 1-3 years, but generally not indefinitely, however an emulsion will not form spontaneously after mixing the aqueous and oil phases and the emulsifier. To form an emulsion an energy input, e.g. via vigorous homogenization, is required.

A special emulsion is the microemulsion, this is dispersion made of aqueous phase, oil phase, and emulsifier(s) that is an isotropic and thermodynamically stable system with dispersed phase globule diameter that does not exceed 350 nm and is usually less than 100 nm. The very small size of dispersed phase globules of a microemulsion is achieved using emulsifiers with specific properties and usually in higher amounts. Owning to the small size of the dispersed phase globules, the microemulsions can appear transparent since the dispersed phase globule size is significantly smaller than the wavelength of the visible light and because of this no or little light scattering occurs. The microemulsions are able to form with little mechanical energy input: to prepare a microemulsion all components are simply added to a vessel and only a mild agitation will be needed to create the microemulsion. The small globule size may promote the skin penetration of skin care ingredients incorporated in the dispersed phase and the transparent appearance of the microemulsion is often aesthetically appealing. For these reasons, microemulsions are gaining in popularity in cosmetic field. Microemulsions also exist as oil-in-water (O/W) or water-in-oil (W/O) systems.

In microemulsions, depending on the amount of the emulsifier in the mixture and the temperature, the micelles may take more complex shapes, such as ellipsoids, cylinders and bilayers. The complex micelles of the microemulsion can organize as various liquid crystalline phases: cubic, hexagonal, lamellar, etc. Owning to the presence of liquid crystals, lamellar lipid bilayer organization, vesicles, worm or sponge like micelles and other structures that can span over macroscopic distances the phases of the microemulsion possess long-range order. Such microemulsion is then a structured liquid. These macrostructures can complicate the rheological behavior since the forces between the macroscopic structures of the microemulsion such as cohesive forces or adhesive forces can have a big impact the rheology of the microemulsion or confer it rheological properties which deviate significantly from the properties of phases. For example, the repulsive and attractive forces between the micelles may lead to microemulsion gelation, even though the microemulsion does not contain a gelling agent and the phases are free flowing liquids.

The cosmetic products can be packaged in variety of packaging, such as jars, tubes, flasks, etc. Desirable, especially from hygiene point of view, are containers from which the product can be withdrawn without the consumer coming in contact with the bulk of the product in the container, for example flasks containing the product that have an opening through which the product can be squeezed out by applying force on the walls of the flask. Another example is containers having a closure with an integrated pump with the help of which the product can be pumped out of the container through the product discharge opening of the pump. To prevent contamination, the diameter of the opening (referred herein as nozzle) is usually much smaller than the diameter of the flask, with typical nozzle diameters laying between 0.1 mm and 10 mm, which corresponds to the circular plane surface area of the nozzle of 0.0079 mm2 to 79 mm2. Nozzles can be of shape other than round but the size of nozzles usually does not exceed 10 mm in any dimension.

Applying shear force to the microemulsion (straining) can store energy in the microemulsion, and the microemulsion can exhibit a variety of elastic effects (behave as viscoelastic fluid). An example of elastic effect is when a viscoelastic liquid is flowing out a container through a small orifice in its bottom. The lower part of the liquid flows out of the orifice however the upper part of the liquid rebounds upwards into the container. Another example of elastic effect is the so called open (tubeless) siphon effect, in which if a jet of liquid is created that raises from the surface of the liquid over the wall of the container the liquid is in, the liquid in the container will be drawn up and over the wall of the container by the elastic forces from the descending liquid. When flowing out a discharge nozzle (so called "die"), after leaving the nozzle the stream of viscoelastic liquid will expand in diameter much beyond the diameter of the nozzle (e.g. 300% increase) resulting in the phenomenon known as the "die swell". The die swell is caused by the released of the elastic energy which is stored in the liquid as it was passing through the nozzle.

The combined effect of the microemulsion being a structured liquid with strong forces within the liquid crystal structures and behaving as visco-elastic fluid means that often the rheology of the microemulsion is very complex and highly unpredictable. Microemulsions can exhibit highly errant rheological behavior during their withdrawal from the container through a nozzle which deviate from desired dispensing, such as the errant jetting, unpredictable squirting or erratic jet rebounding from the surface of the already withdrawn product. Improper droplet atomization, for example the dispensing of long tubes of low viscosity microemulsion which do not atomize into droplets is observed and is not desired. Especially unappealing is when the internal cohesive forces in the microemulsion result in creation of gooey strands which raise from the liquid upon picking up the product with the finger or hang on the pump after dispensing. These effects can present themselves on the consumer scale even though the liquid is flowable or pumpable on the industrial scale.

Known from U.S. Pat. Nos. 4,797,272, 8,852,648 or WO2005/020938 are various forms of cosmetic microemulsion systems but these documents do not describe a rational way to produce microemulsions with desired rheological behavior.

Known from WO2002/043674, WO2004/091565, US20110033512, U.S. Pat. No. 5,686,087, JP2004075639 or JP09-151112A are microemulsions whose spreadability allows the creation of the desired texture (the structural character of the microemulsion perceived by touch) or after-feel after application on the skin, but neither texture or after feel are predictive of the rheological behavior, and microemulsion of same texture or same after-feel can have varied rheological behaviors and conversely two microemulsions that exhibit same or similar rheological behavior can have a profoundly different texture or leave different after-feel.

Known from DE10361568 is cosmetic preparation characterized by having a slidability after 5 minutes of above 6 (as determined by the spectrum method described in that document) which is based on an emulsion which comprises: (a) a lipid of viscosity 10 mPas and/or spreadability 3>700 (especially 3>1000) mm2/minute; and (b) below 3 (especially 0) wt. % cyclomethicone, especially cyclopentasiloxane and/or cyclohexasiloxane to achieve a desired preparation spreadability on the skin. However, the spreadability on the skin is not predictive of the rheological behavior since microemulsion of same skin spreadability can have varied rheological behaviors.

Known from EP1147760 are water-in-oil emulsions with a water phase content of at least 80 wt. % containing: (A) a lipid phase containing a lipid of viscosity below 15 mPa·s at 25 degrees C. and of spreading value >=700 mm2/10 minutes at 25 degrees C.; (B) a surfactant of formula (I) and optionally (C) a cationic, nonionic and/or anionic polymer at preferably 0.01-10 (especially 0.1-5) wt. %. A and A'=optionally unsaturated 10-30 C alkyl, acyl or hydroxyacyl or an ester-bonded hydroxyacyl group of formula (II); R'=1-20 C alkyl; R"=1-20 C alkylene; a=1-100 (especially 5-40); b=0-200; X=a bond or —CH(OR3)-; R1 and R2=H or Me; and R3=H or 1-20 C optionally unsaturated alkyl or acyl to achieve a low viscosity preparation. However, owned to the unpredictable rheology of structured liquid and the visco-elascic behavior, viscosity alone is insufficient to describe the rheological behavior of microemulsions as viscous microemulsions can have a good rheological behavior and a low viscosity or substantially non-viscous microemulsions can exhibit erratic rheological behavior.

Known from WO2013/120829 is a flowable (defined as having a viscosity of less than 4000 mPas at 20° C.) water in oil emulsion comprising at least two W/O emulsifiers and one and more oils having a spreadability value greater than 600 mm2/10 min. WO2013/120829 describes ways to adjust the viscosity of the cosmetic water in oil emulsions by incorporating oils with spreadability value greater than 600 mm2/10 min, however flowability (expressed as low viscosity) alone is insufficient to predict the rheological behaviour as low flowable (viscous) microemulsions can have a good rheological behavior and highly flowable (low viscosity or substantially non-viscous microemulsions) can exhibit erratic rheological behavior.

Known from WO02/102327 is a microemulsion composition comprising: (a) 5 to 30% by wt. microemulsion of an oil or oils which dissolve at least 20% triolein and which have spreadability factor SR (ratio of spreading time in minutes of selected oil to spreading time in minutes of oleyl oleate) of greater than 0.3 to less than 2.5; (b) 5 to 40% by wt. microemulsion of a surfactant selected from the group consisting of anionic, nonionic amphoteric/zwitterionic, cationic and mixtures thereof; (c) 1 to 15% microemulsion of water-soluble co-surfactant comprising C2-C10 straight or branched chain alcohol; (d) 0 to 30% water soluble polyalcohol or humectant; and (e) balance water with superior cleansing effect and not too oily. In the paragraph [0137], WO02/102327 describes the measurement of surface tension of microemulsion by drop volume method and in paragraph [0142], WO02/102327 describes the use of ARES Rheometer to measure viscosity of the microemulsion. As described previously, viscosity alone is insufficient to predict the rheological behavior of microemulsions. Surface tension is another physicochemical parameter loseses its prediction value in the structured liquids, such as microemulsions, since the influence of surface tension may be superseded by the internal cohesive forces of the microemulsions as described previously.

Known from EP1889596 is an oil-in-water cosmetic preparation that comprises one or more polyol, light-weight oils with a viscosity of 1-15 mPas and a spreading coefficient of 800-1200 mm2/10 minutes, medium-weight oils with a viscosity of 20-100 mPas and a spreading coefficient of 300-600 mm2/10 minutes and wax with a melting point of 25-45° C., however, EP1889596 does not describe a rational way to produce microemulsions with desired rheological behavior.

Known for example from U.S. Pat. Nos. 4,371,447, 4,472,291, WO 95/06102 or EP1813251 are ways to produce microemulsions with specific viscosity (low, high or within certain range), however, owned to the unpredictable rheology of structured liquid and the visco-elascic behavior, specific viscosity alone is insufficient to describe the rheological behavior of microemulsions as viscous microemulsions can have a good rheological behavior or exhibit a behavior which is predictable to the consumer, low viscosity or substantially non-viscous microemulsions can exhibit erratic rheological behavior and a microemulsion can exhibit errant rheological behavior even if its viscosity is within a certain range.

US2006/0193810 teaches that when polyvinyl pyrrolidone polymers are used as an ingredient of a microemulsion, the Mw of polyvinyl pyrrolidone polymers should preferably not exceed 500000 as higher Mw may affect the viscosity of the system. The document does not state in what way the polyvinyl pyrrolidone polymers with MW higher than 500000 will affect the viscosity. Also, this document states that when the content of polyvinyl pyrrolidone polymers in the microemulsion exceeds 40% by weight, the viscosity of the system increases excessively and worsens the property in use. The document does not state what constitutes "excessive increase". Controlling the viscosity of the microemulsion by excluding or limiting the concentration of certain ingredients is not sufficient to produce microemulsions with desired rheological behavior since, as stated previously, the viscosity alone is not a good predictor of rheological behavior in complex systems, such as microemulsions.

Known from U.S. Pat. No. 6,291,418, WO/2009/080657, U.S. Pat. Nos. 6,362,155, 7,176,174 US2010009873, US2011177019 or U.S. Pat. No. 8,404,218B are various ways to thicken or to gel the microemulsion (e.g. with salt, starch, thickeners, polysaccharides, agars, polyisobutene, polyacrylate, polymethacrylate, etc.). Thickening is usually done to increase the viscosity of the product and sometimes to increase the stability of the emulsion. As described previously, viscosity alone is insufficient to predict the rheological behavior of microemulsions and stable emulsions can exhibit errant rheological behavior and vice versa.

Known from US20050232974 is a jettable solution comprising: an oil, said oil being one of a naturally occurring oil, an edible oil, or a removable oil; an edible surfactant; an edible aqueous solution; and a pharmaceutical solubilized into said oil; wherein said oil, said pharmaceutical, said surfactant, and said aqueous solution form a microemulsion. In this document, the term "jettable" is meant to be understood as any material that has properties sufficient to allow the material to be selectively deposited by any digitally addressable inkjet material dispenser. However, US20050232974 only describe the viscosity of the microemulsion as a means to control jettability. This may be sufficient for selective depositing of nanometer size liquid droplets by a digitally addressable inkjet material dispenser, however as described previously viscosity alone is insufficient to describe the rheological behavior of microemulsions on a consumer scale.

Known from WO/2005/102256, U.S. Pat. No. 7,781,489, US2015/0011654, EP1639989 or WO/2005/105027 are rheological characterizations of microemulsions but the rheological characterization described in these documents is limited to measuring the viscosity and these documents do not describe a rational way to produce microemulsions with desired rheological behavior.

Known from EP2343036A1 are oil in water nanoemulsions containing one or more nonionic amphiphilic lipids, one or more volatile linear alkanes and one or more oils other than the volatile linear alkanes. According to the Table 2 of EP2343036A1, the volatile linear alkanes resulted in greater thickening of the microemulsion system than cyclopentadimethylsiloxane. Since both volatile linear alkanes (undecane/tridecane mixture) and cyclopentadimethylsiloxane are low viscosity substances (viscosity of both <4 cP), it is not clear from this document how to control the viscosity of the nanoemulsion. Also EP2343036A1 does not describe a rational way to produce microemulsions with desired rheological behavior.

W/O microemulsions which exhibit errant rheological behavior are difficult to handle and cannot be offered in packaging that permit forcible product withdrawal from the container through a nozzle or small opening (such as squeeze bottle) and only can be offered in packaging such as roll-ons for spreading on the skin or pre-portioned one-use ampules. Clearly the known ways to produce W/O microemulsions with desired rheological behavior are not satisfactory. There is thus still a need for a W/O microemulsion which do not exhibit the aforesaid disadvantages.

Hence the problem to solve is to create a W/O microemulsion lying within the technological field stated at the outset, that enable a simple and user-friendly handling.

The solution to the problem is defined by the characteristics of claim 1. According to the invention is a cosmetic W/O microemulsion comprising: i) 20-40% w/w of oil phase ingredient(s) with spreadability value above 1700 mm2/10 min at 25° C., ii) 15-35% w/w of oil phase ingredient(s) with spreadability value between 1000 and 1700 mm2/10 min at 25° C., iii) 1-15% w/w of oil phase ingredient(s) with spreadability value between 500 and 999 mm2/10 min at 25° C., iv) 0-10% w/w of oil phase ingredient(s) with spreadability value below 500 mm2/10 min at 25° C., v) 0.2-15% w/w of co-surfactant(s) selected from glycerin, propylene glycol, 1,10-decanediol, 1,2-butanediol, 1,3-butanediol, 1,2-hexanediol, 1,4-butanediol, 1,5-pentanediol, 2,3-butanediol, hexanediol, ethyl hexanediol, isopentyldiol, methylpropanediol, propanediol, butylene glycol, dipropylene glycol, glycol, hexylene glycol, neopentyl glycol, pentylene glycol, 1,2,6-hexanetriol, mannitol, erythritol, xylitol or sorbitol, vi) 0-10% w/w of co-solvent(s) selected from ethanol, 1-propanol or 2-propanol, vii) 5-30% w/w of fatty acid ester(s) of glycerol or fatty acid ester(s) of polyglycerol, viii) 5-20% w/w of water. This W/O microemulsion has advantageous rheological behavior, in particular advantageous dispensability which is demonstrated by the fact that the W/O microemulsion is dispensable at a constant flow rate of 0.05 ml/sec from a nozzle pipe orifice of a vertically positioned nozzle pipe with a length of 15 mm and an inner diameter of 2 mm and the height of any of the pending drops that hang on the nozzle pipe orifice does not exceed 10 mm for at least 180 consecutive seconds at ambient conditions.

The cosmetic W/O microemulsion according to the invention is dispensable from the container through a nozzle of various shapes that have cross-sectional area from 0.0079 mm2 to 79 mm2 in a way which is easy to handle, meaning for example that upon forcing the W/O microemulsion out of the container (e.g. by squeezing the container) through a nozzle, the product will flow out of the nozzle in the direction the nozzle is pointed to, the product will atomize into droplets in a way which correlates to its viscosity (for example runny products are expected to create smaller droplets, whereas thick products are expected not to atomize easily) and will not exhibit strong internal cohesive forces which will result to the appearance of gooey product strands.

The cosmetic W/O microemulsion according to the invention is dispensable from a container through a nozzle in 0.02-10 ml portions in a way which is easy to handle. The 0.02 ml-10 ml portions are portions in which the cosmetic products are typically withdrawn from a container. For example, 0.02 ml-10 ml is typically the amount withdrawn per stroke of pump piston or plunger or typically the amount per squeeze out from a plastic bottle. A consumer can typically dispense one or several portions.

The time it takes for a consumer to dispense one cosmetic product portion of 0.02 ml-10 ml from a container through a nozzle typically does not exceed few seconds and usually is one or two seconds. Knowing this, and depending on the expected portion of product to be dispensed and to minimize the effort from the side of the consumer, the nozzles are dimensioned appropriately, with packaging of product that is expected to be dispensed in smaller amounts having nozzles with smaller cross-sectional area and product that is expected to be dispensed in larger amounts having nozzles with larger cross-sectional area. The flow of various portions of liquid through the nozzle of various cross-sectional area within a certain time span is better described using the volumetric flux, which is the rate of volume flow across a unit area, expressed as volume/(second*area) or as volume per second per area. The cosmetic W/O microemulsion according to the invention can be dispensed from the container at volumetric flux from 0.01 ml per second per mm2 to 25.0 ml per second per mm2 in a way which is easy to handle.

Forced through a nozzle at volumetric flux from 0.01 ml per second per mm2 to 25.0 ml per second per mm2 (consumer scale) the liquids present special rheological behavior, especially special dispensability behavior, compared for example to the rheological behavior on a very small (e.g. nanoliters) scale or on a large scale.

It has been surprisingly found, that by testing the dispensability of the W/O microemulsion in one particular setting involving dispensing the W/O microemulsion for 180 seconds at ambient conditions at a constant flow rate of 0.05 ml/sec from a nozzle pipe orifice of a vertically positioned nozzle pipe with a length of 15 mm and an inner diameter of 2 mm and selecting W/O microemulsions whose drops detach from the nozzle pipe orifice before the height of any of the pending drops reaches 10 mm for the entire test duration of 180 seconds it is possible to select W/O microemulsions with good dispensability properties and the selected W/O microemulsions can be easily dispensed at volumetric fluxes from 0.01 ml per second per mm2 to 25.0 ml per second per mm2, from nozzles of various shapes having cross-sectional area from 0.0079 mm2 to 79 mm2 and in portions from 0.02 ml to 10 ml, which facilitates handling.

The testing device to test the dispensability of the W/O microemulsion comprises a pump able to pump the W/O microemulsion at a constant flow rate of 0.05 ml/sec, a vertically positioned nozzle pipe with a length of 15 mm and an inner diameter of 2 mm, an outlet tube connected with one of it ends to the pump outlet and is connected with another end to the nozzle pipe and means to measure the height of the pending drops for entire test duration of 180 seconds. One embodiment of the testing device is depicted in FIG. 1. Alternative embodiments comprise dispensing the W/O microemulsion using a metering syringe pump or using manual pumps with integrated nozzle pipe, such as a transfer pipette.

Using the testing device, when the W/O microemulsion is dispensed at a constant flow rate of 0.05 ml/sec from a nozzle pipe orifice of a vertically positioned nozzle pipe with a length of 15 mm and an inner diameter of 2 mm and the height of the pending drops that hang from the nozzle pipe orifice does not exceed 10 mm for the entire test duration of 180 seconds then the W/O microemulsion possesses good dispensability properties and can be easily dispensed at volumetric fluxes from 0.01 ml per second per mm2 to 25.0 ml per second per mm2, from nozzles of various shapes having cross-sectional area from 0.0079 mm2 to 79 mm2 and in portions from 0.02 ml to 10 ml, which facilitates handling.

The advantage of the W/O microemulsion according to the invention is that the structure of the emulsion is adjusted in such a way that it is dispensable and possesses improved rheological behavior. This enables the use of wide variety of dispensing procedures and devices, such as dispensing from a dosing pump, dispensing from a dosing pipette, dispensing from a spray-head, etc. Additionally, the W/O microemulsion according to the invention can be dispensed with means for dispensing made of various materials, such as glass, plastics or metals. Finally, owned to improved rheological behavior, the W/O microemulsion according to the invention is more pleasant in handling when picked up from a jar or crucible since due to improved atomization the gooey strands or long product tubes are not being created.

Another advantage of the W/O microemulsion according to the invention is that it provides a rational way to produce W/O microemulsions with good dispensability.

Another advantage of the W/O microemulsion according to the invention is good droplet atomization during the dispensing, whereby the W/O microemulsion easily produces discrete and separate droplets, which eases handling.

Another advantage of the W/O microemulsion according to the invention that it does not produce gooey produce strands, which eases handling.

Another advantage of the W/O microemulsion according to the invention is that it can be packaged in containers from which it can be forcibly dispensed through a nozzle or small opening, for example using a cosmetic pump.

In another embodiment, the cosmetic W/O microemulsion as recited in claim 1 is characterized in that the ingredients i through viii listed in claim 1 add up to a total of at least 95% w/w relative to the total weight of the W/O microemulsion. The advantage of the W/O microemulsion according to this embodiment is that it represents a rational way to produce W/O microemulsions with good dispensability.

It has been surprisingly found that W/O microemulsion dispensable at a constant flow rate of 0.05 ml/sec from a nozzle pipe orifice of a vertically positioned nozzle pipe with a length of 15 mm and an inner diameter of 2 mm and the height of any of the pending drops that hang on the nozzle pipe orifice does not exceed 10 mm for at least 180 consecutive seconds at ambient conditions can be produced by carefully controlling the amount and the spreadability value of ingredients of the oil phase.

The spreading pressure is a measure of the tendency of a liquid phase to spread on a solid surface and is expressed as the difference between the work of adhesion between the liquid and a solid surface and the work of cohesion within the liquid. Positive values for the spreading pressure (also known as spreading coefficient) mean that the liquid will spread on the solid. In the cosmetic field, the spreading coefficient is often being referred to as the spreadability value on the skin and is expressed in area in square millimeters (denoted in this text as mm2) covered by the spreading liquid per 10 minutes. The determination of the spreadability value was first described by U. Zeidler in the Journal Fats, Soaps, Paints 87, 403 (1985). U. Zielder used the spreadability value to correlate the subjective feeling of an emollient on the skin with the physicochemical parameters of the spreading of the emollient on the surface of the skin. According to U. Zeidler, the substances can be classified as having low spreadability value (below 300 mm2/10 min), medium spreadability value (300-1000) and high spreadability value (>1000 mm2/min). For the purposes of this invention, a method which is deviating from the method used by U. Zielder is used. Instead of spreading on the skin, the tests use spreadability on a filter paper at 25° C. For the test, the following filter paper is used: grade 589/5, red ribbon, material: cellulose, properties: medium-slow, retention range: 2-4 μm, weight: 85 g/m2, thickness: 0.17 mm, filtration time to Herzberg: 450 s, filtration time to DIN 53 137: 35-90 s, 125 mm in diameter, product brand name Whatman® (formerly Schleicher & Schuell), sold by the company Sigma-Aldrich. At 25° C.+/−1° C., 20 microliters of the oil are dispensed into the middle of the filter paper and simultaneously a timer is started. After 10 minutes, the area which is wetted by the oil is measured and the spreadability value is expressed as mm2/10 min. For the purposes of evaluation, advantageously a photographic camera is used to take a picture of the filter paper for subsequent evaluation.

The spreadability values obtained in different laboratories may differ from one given here, due to variability of filter papers and other factors. For comparison purposes, the spreadability values of the following four substances should be determined at 25° C. using the filter paper method described herein: oleyl erucate (spreadability value 350 mm2/10 min), cetearyl isononanoate (spreadability value 700 mm2/10 min), isopropyl myristate (spreadability value 1200 mm2/10 min), propylheptyl caprylate (spreadability 1900 mm2/10 min) and the results used to calculate a correction factor that will position the substance within the spreadability value categories as described in the current text.

For the purpose of this invention and in deviation to the original classification of U. Zeidler, the following classes of the spreadability value are used (obtained using the filter paper method described herein):
Low spreadability value: below 500 mm2/10 min at 25° C.
Medium spreadability value: 500 to 999 mm2/10 min at 25° C.
High spreadability value: 1000 to 1700 mm2/10 min at 25° C.
Very High spreadability value: above 1700 mm2/10 min at 25° C.

According to the current invention, the spreadability value can be used as a summary value of various physico-chemical properties of an ingredient, such as for example surface tension, viscosity, relative molecular weight, volatility, etc. and a guide value for preparing the W/O microemulsions with desirable dispensability properties. Thus, the work to obtain the W/O microemulsion with desired dispensability properties is greatly simplified.

The W/O microemulsion according to the invention comprises an oil phase, an aqueous phase, emulsifier(s), co-surfactant(s), optionally one or more polar co-solvent(s), optionally one or more cosmetic active ingredient(s), optionally one or more skin care ingredients optionally at least one water-soluble extract of plant material and optionally one or more cosmetic auxiliary ingredient(s).

According to International Union of Pure and Applied Chemistry, chemical substance or substance is a form of matter that has constant chemical composition and characteristic properties. It cannot be separated into components by physical separation methods, i.e., without breaking chemical bonds. Chemical substances can be chemical elements, chemical compounds, ions or alloys. An ingredient is a substance that is part of the mixture of substances. A cosmetic ingredient is a substance which is part of a cosmetic composition, i.e. a mixture of cosmetic substances. A skin care ingredient is defined as any substance which is generally recognized as safe for application on the skin and possess at least one desirable quality in the area of skin care.

The oil phase according to the invention obligatory comprises oil phase ingredient(s) with very high spreadability value (above 1700 mm2/10 min at 25° C.), obligatory comprises oil phase ingredient(s) with high spreadability value (1000 to 1700 mm2/10 min at 25° C.), obligatory comprises oil phase ingredient(s) with medium spreadability value (500 to 999 mm2/10 min at 25° C.) and optionally comprises oil phase ingredient(s) with low spreadability value (below 500 mm2/10 min at 25° C.).

Oil phase ingredients with very high spreadability value (above 1700 mm2/10 min at 25° C.) include for example linear hydrocarbons (alkanes) with chains length of 11 (undecane), 12 (dodecane), 13 (tridecane) or 14 (tetradecane) carbon atoms, as well as branched hydrocarbons such as isohexadecane as well as propylheptyl caprylate, hydrogenated polyisobutene, etc.; this list being non exhaustive. Undecane (CAS 1120-21-4) and tridecane (CAS 629-50-5) are available as a mixture under the trade name CETIOL® ULTIMATE from company BASF. Dodecane (CAS 112-40-3) is available for example under the trade name MAKI-GREEN D10 from the company Daito Kasei Kogyo. Tetradecane is available for example under the trade name PARAFOL 14-97 from the company Sasol Performance Chemicals. Isohexadecane is available for example under the trade name Arlamol™ HD from the company Croda. Propylheptyl Caprylate (CAS 868839-23-0) is available for example under the trade name Cetiol® Sensoft from the company BASF. Hydrogenated Polyisobutene (CAS 90622-59-6) is available for example under the trade name Luvitol® Lite from the company BASF.

According to the invention, the amount the oil phase ingredients with very high spreadability value (above 1700 mm2/10 min at 25° C.) is between 20% w/w and 40% w/w of the total weight of the W/O microemulsion. In another embodiment, the amount the oil phase ingredients with very high spreadability value (above 1700 mm2/10 min at 25° C.) in the W/O microemulsion is preferably between 22% w/w and 35% w/w of the total weight of W/O microemulsion. In another embodiment, the amount the oil phase ingredients with very high spreadability value (above 1700 mm2/10 min at 25° C.) in the W/O microemulsion is preferably between 24% w/w and 30% w/w of the total weight of the W/O microemulsion. In another embodiment, the cosmetic W/O microemulsion as recited in one of claims 1 and 2, characterized in that the oil phase ingredients with spreadability value above 1700 mm2/10 min at 25° C. are selected from undecane, dodecane, tridecane, tetradecane, isohexadecane, propylheptyl caprylate and hydrogenated polyisobutene. These ingredients are particularly suitable to achieve the advantages described herein and also help to create the light after feel on the skin after application of the cosmetic W/O microemulsion on the skin.

Oil phase ingredients with high spreadability value (1000 to 1700 mm2/10 min at 25° C.) include for example hexyl laurate, dibutyl adipate, coco-caprylate, dicaprylyl carbonate, dicaprylyl ether, caprylyl caprylate/caprate, isopropyl myristate, isopropyl palmitate, isoamyl laurate, etc.; this list being non exhaustive. Hexyl laurate (CAS 34316-64-8) is available for example under the trade name Cetiol® A from the company BASF. Dibutyl adipate (CAS 105-99-7) is available for example under the trade name Cetiol® B from the company BASF. Coco-caprylate (CAS 107525-85-9) is available for example under the trade name SABODERM CV from the company SABO S.p.A. Dicaprylyl carbonate (CAS 1680-31-5) is available for example under the trade name Lonzest® DC NT Emollient Ester from the company Lonza. Dicaprylyl ether (CAS 629-82-3) is available for example under the trade name SABODERM DOE from the company SABO S.p.A. Caprylyl caprylate/caprate (CAS 2306-88-9 and 2306-92-5) is available for example under the trade name Cetiol® RLF from the company BASF. Isopropyl Myristate (CAS 110-27-0) is available for example under the trade name BergaCare EM-14 from the company Berg+Schmidt GmbH & Co. KG. Isoamyl laurate (CAS 6309-51-9) is available for example under the trade name Dermofeel® sensolve from company Dr. Straetmans. Isopropyl palmitate (CAS 142-91-6) is available for example under the trade name BergaCare EM-16 from the company Berg+Schmidt GmbH & Co. KG.

According to the invention, the amount the oil phase ingredients with high spreadability value (1000 to 1700 mm2/10 min at 25° C.) is between 15% w/w and 35% w/w of the total weight of the W/O microemulsion. In another embodiment, the amount the oil phase ingredients with high spreadability value (1000 to 1700 mm2/10 min at 25° C.) in the W/O microemulsion is preferably between 17% w/w and 30% w/w of the total weight of the W/O microemulsion. In another embodiment, the amount the oil phase ingredients with high spreadability value (1000 to 1700 mm2/10 min at 25° C.) in the W/O microemulsion is preferably between 19% w/w and 25% w/w of the total weight of W/O microemulsion.

In another embodiment, the cosmetic W/O microemulsion as recited in one of claims 1 through 3, characterized in that the oil phase ingredients with spreadability value between 1000 and 1700 mm2/10 min at 25° C. are selected from hexyl laurate, dibutyl adipate, coco-caprylate, dicaprylyl carbonate, dicaprylyl ether, caprylyl caprylate/caprate, isopropyl myristate, isopropyl palmitate and isoamyl laurate. These ingredients are particularly suitable to achieve the advantages described herein and also help in quick spreading of the cosmetic W/O microemulsion on the skin.

Oil phase ingredients with medium spreadability value (500 to 999 mm2/10 min at 25° C.) include for example ethylhexyl palmitate, ethylhexyl stearate, coco-caprylate/caprate, diethylhexylcyclohexane, cetearyl isononanoate, decyl oleate, octyldodecanol, hexyldecanol, cetearyl ethylhexanoate, caprylic/capric Triglyceride, cocoglycerides, propylene glycol dicaprylate/dicaprate, etc.; this list being non exhaustive. Ethylhexyl palmitate (CAS 29806-73-3) is available for example under the trade name TEGOSOFT® OP from the company Evonik Industries AG Personal Care. Ethylhexyl stearate (CAS 91031-48-0 or 22047-49-0 or 29806-73-3.) is available for example under the trade name Cetiol® 868 from the company BASF. Coco-Caprylate/Caprate (CAS 95912-86-0) is available for example under the trade name DUB 810 C from the company SEPPIC. Diethylhexylcyclohexane (CAS 84753-08-2) is available for example under the trade name Cetiol® S from the company BASF. Cetearyl isononanoate (CAS 84878-33-1 or 84878-34-2 or 111937-03-2) is available for example under the trade name Cetiol® SN from the company BASF. Decyl oleate (CAS 3687-46-5) is available for example under the trade name Cetiol® V from the company BASF. Octyldodecanol (CAS 5333-42-6) is available for example under the trade name TEGOSOFT® G 20 from the company Evonik Industries AG Personal Care. Hexyldecanol (CAS 2425-77-6) is available for example under the trade name ISOFOL 16 from the company Sasol Performance Chemicals. Cetearyl ethylhexanoate (CAS 59130-69-7) is available for example under the trade name Schercemol™ 1688 Ester from the company Lubrizol. Caprylic/Capric Triglyceride (CAS 73398-61-5) is available for example under the trade name SABODERM TCC from the company SABO S.p.A. Cocoglycerides (CAS 68606-18-8) is available for example under the trade name Myritol® 331 from the company BASF. Propylene Glycol Dicaprylate/Dicaprate (CAS 68583-51-7 or 58748-27-9 or 68988-72-7) is available for example under the trade name Crodamol™ PC from the company Croda.

According to the invention, the amount the oil phase ingredients with medium spreadability value (500 to 999 mm2/10 min at 25° C.) is between 1% w/w and 15% w/w of the total weight of the W/O microemulsion. In another embodiment, the amount the oil phase ingredients with medium spreadability value (500 to 999 mm2/10 min at 25° C.) in the W/O microemulsion is preferably between 2% w/w and 10% w/w of the total weight of the W/O microemulsion. In another embodiment, the amount the oil phase ingredients with medium spreadability value (500 to 999 mm2/10 min at 25° C.) in the W/O microemulsion is preferably between 3% w/w and 6% w/w of the total weight of the W/O microemulsion.

In another embodiment, the cosmetic W/O microemulsion as recited in one of claims 1 through 4, characterized in that the oil phase ingredients with spreadability value between 500 and 999 mm2/10 min at 25° C. are selected from ethylhexyl palmitate, ethylhexyl stearate, coco-caprylate/caprate, diethylhexylcyclohexane, cetearyl isononanoate, decyl oleate, octyldodecanol, hexyldecanol, cetearyl ethylhexanoate, caprylic/capric triglyceride, cocoglycerides and propylene glycol dicaprylate/dicaprate. These ingredients are particularly suitable to achieve the advantages described herein and also help to convey the feeling of substance and sufficiency (the feeling that enough product has been applied for the desired purpose) after application of the cosmetic W/O microemulsion on the skin. Oil phase ingredients with low spreadability value (below 500 mm2/10 min at 25° C.) include for example *Elaeis guineensis* Oil, *Passiflora incarnata* Seed Oil, Olus Oil, C12-15 Alkyl Benzoate, Polyoxypropylene 15 stearyl ether, 13-docosenoic acid, 9-octadecenyl ester, Hexyldecyl Stearate, triisostearin and others; this list being non exhaustive. *Elaeis guineensis* Oil (CAS 8002-75-3) is available for example under the name Palm Oil from the company Gustav Heess GmbH in Leonberg, Germany. *Passiflora incarnata* Seed Oil (CAS 97676-26-1 or 72968-47-9) is available for example under the trade name Cegesoft® PFO from the company BASF. Olus Oil (CAS 68956-68-3) is available for example under the trade name Cremerlin® PURA from the company CREMER OLEO. C12-15 Alkyl Benzoate (CAS 68411-27-8) is an ester of benzoic acid and C12-15 alcohols and is available for example under the trade name Finsolv® TN or Finsolv® TN-O from company Innospec Performance Chemicals. Polyoxypropylene 15 stearyl ether (CAS 25231-21-4) or PPG-15 Stearyl Ether is available for example under the trade name Sympatens-ASP/100 or Sympatens-ASP/150 from company Kolb in Hedingen, Switzerland. 13-Docosenoic acid, 9-octadecenyl ester (CAS 17673-56-2) is an ester of erucic acid and oleyl alcohol and is available for example under the trade name TEGOSOFT® OER from the company Evonik Industries AG Personal Care. Hexyldecyl stearate (CAS 101227-09-2) is available for example under the trade name Eutanol® G 16 S from company BASF.

According to the invention, the oil phase ingredients with low spreadability value below 500 mm2/10 min at 25° C.) are optional. In another embodiment, the oil phase ingredients with low spreadability value (below 500 mm2/10 min at 25° C.) according to the invention are absent. In another embodiment, the amount the oil phase ingredients with low spreadability value (below 500 mm2/10 min at 25° C.) is preferably between 0.1% w/w-10% w/w of the total weight of W/O microemulsion. In another embodiment, the amount the oil phase ingredients with low spreadability value (below 500 mm2/10 min at 25° C.) is preferably between 0.2% w/w-8% w/w of the total weight of W/O microemulsion. In another embodiment, the amount of the oil phase ingredients with low spreadability value (below 500 mm2/10 min at 25° C.) is preferably between 0.5% w/w-5% w/w of the total weight of W/O microemulsion.

In another embodiment, the cosmetic W/O microemulsion as recited in one of claims 1 through 5, is characterized in that the oil phase ingredients with spreadability value below 500 mm2/10 min at 25° C. are selected from *Elaeis guineensis* oil, *Passiflora incarnata* seed oil, olus oil, C12-15 Alkyl Benzoate, polyoxypropylene 15 stearyl ether, 13-docosenoic acid, 9-octadecenyl ester, hexyldecyl stearate and triisostearin. These ingredients are particularly suitable to achieve the advantages described herein and also help to create the long-term after feel on the skin after application of the cosmetic W/O microemulsion on the skin.

According to the invention, the sum of the amount the oil phase ingredients with medium spreadability value (500 to 999 mm2/10 min) and low spreadability value (below 500 mm2/10 min) does not exceed 15% w/w of the total weight of the W/O microemulsion. In another embodiment, the sum of the amount the oil phase ingredients with medium spreadability value (500 to 999 mm2/10 min) and low spreadability value (below 500 mm2/10 min) is preferably between 1% w/w and 15% w/w of the total weight of the W/O microemulsion. In another embodiment, the sum of the amount the oil phase ingredients with medium spreadability value (500 to 999 mm2/10 min) and low spreadability value (below 500 mm2/10 min) is preferably between 2% w/w and 13% w/w of the total weight of W/O microemulsion. In another embodiment, the sum of the amount the oil phase ingredients with medium spreadability value (500 to 999 mm2/10 min) and low spreadability value (below 500 mm2/10 min) is preferably between 3% w/w and 10% w/w of the total weight of the W/O microemulsion.

Generally, plant oils (also known as vegetable oils) have a low spreadability value. A non-exhaustive list of examples of vegetable oils is *Adansonia digitata* Seed Oil, Apricot kernel oil, Almond oil, Sweet Almond oil, Argan oil, *Astrocaryum vulgare* Kernel Oil, Avocado oil, Babassu Oil, *Bertholletia excelsa* Seed Oil, *Carapa guaianensis* Seed Oil, *Citrullus lanatus* (Watermelon) Seed Oil, Cotton seed oil, *Coffea arabica* (Coffee) Seed Oil, Borage oil, Groundnut oil, Evening primrose oil, Pomegranate seed oil, *Ricinus communis* (Castor) Seed Oil, Rosehip seed oil, Hemp oil, Hazelnut oil, Jojoba oil, Coconut oil, Linseed oil, Macadamia nut oil, Maize-germ oil, *Mauritia flexuosa* seed oil, Almond oil, MCT-oil, Olive oil, *Parinari curatellifolia* seed oil, Palm kernel oil, Palm oil, Paraffin oil, Peach kernel oil, *Pinus Sibirica* Seed Oil, Pistachio oil, Pumpkin seed oil, *Rosa Rubiginosa* Seed Oil, Sunflower oil, Rice oil, *Theobroma cacao* (Cocoa) Seed Butter, *Schinziophyton rautanenii* Kernel Oil, *Sesamum indicum* (Sesame) Oil, *Glycine Soja* (Soybean) Oil, *Sclerocarya birrea* Seed Oil, Rapeseed oil (Colza oil), Rice germ oil, Castor oil, Safflower oil, Sesame oil, Soya oil, Sunflower oil, Grapeseed oil, Walnut oil, Wheatgerm oil or *Ximenia americana* Seed Oil.

Wax is a collective name for a diverse class of hydrophobic organic substances whose molecules contain long alkyl chains and which are soft solids at lower temperatures but can melt above about 25-40° C. to a liquid. Waxes are produced by plants and animals and can also be of mineral and synthetic origin. Plant waxes include for example *Acacia decurrens* Flower Wax, *Simmondsia chinensis* (Jojoba) Seed Wax, *Helianthus annuus* (Sunflower) Seed Wax, *Euphorbia Cerifera* (Candelilla) Wax, *Simmondsia chinensis* (Jojoba) Seed Wax, *Oryza sativa* (Rice) Bran Wax. Animal waxes are for example Beeswax or Lanolin. The exact chemical composition of the wax varies from organism to organism and can differ from species to species and also vary according to the geographic location. Example of mineral wax are Montan wax, which is a fossilized wax obtained from coal and petroleum derived waxes. Waxes can be chemically modified or synthesized to obtain synthetic waxes. The W/O microemulsion according to the invention can comprise waxes provided these are dissolved in the oil phase. For the purposes of this invention, waxes are then considered to have low spreadability value.

In another embodiment, the cosmetic W/O microemulsion as recited in one of claims 1 through 6 is characterized in that the oil phase ingredients with spreadability value below 500 mm2/10 min at 25° C. are oils of plant origin or waxes of plant origin. The use of oils of plant origin or waxes of plant origin enables the exploitation of their favorable skin care properties in a product.

Advantageously, the oil phase ingredients with very high spreadability value (above 1700 mm2/10 min and above) have viscosity at 20° C. from about 1 to about 5 mPa s; the oil phase ingredients with high spreadability value (1000 to 1700 mm2/10 min) have viscosity at 20° C. from about 4 to about 10 mPa s; the oil phase ingredients with medium spreadability value (500 to 999 mm2/10 min) have viscosity at 20° C. from about 10 to about 65 mPa s and the oil phase ingredients with low spreadability value (below 500 mm2/10 min) have viscosity at 20° C. from about 30 to about 100 mPa s.

The W/O microemulsion according to the invention comprises an emulsifier.

A degree to which an emulsifier is hydrophilic or lipophilic can be categorized according to their hydrophilic-lipophilic balance (HLB) value of the emulsifier, which can be calculated according to the Griffins method as HLB=20* [molecular mass of hydrophilic portion of the molecule]/ [molecular mass of the whole molecule], which gives results from 0 to 20. HLB value can generally be used to select most appropriate emulsifier for the particular application, with HLB values of 3-8 being generally more appropriate for W/O emulsifiers and HLB values of 8-15 being generally more appropriate for O/W emulsifiers. Advantageously, W/O emulsifiers with HLB values of 8-15 are selected.

An emulsifier can advantageously be selected using the Phase Inversion Temperature (PIT) method. For this, equal parts of oil and aqueous phase are added together as well as 5% of emulsifier. At the PIT temperature of the microemulsion the hydrophilic and the lipophilic propensities of the emulsifier are balanced. When the emulsifier yields a PIT in the area of 40-90° C., this emulsifier is generally more suitable for O/W emulsion. When the emulsifier yields a PIT in the area of 5-35° C. than this emulsifier is generally more suitable for W/O emulsion. Advantageously, W/O emulsifiers with PIT values 5-35° C. are selected.

Many various substances can serve as emulsifier in a W/O microemulsion system, for example block copolymers of ethylene oxide or block copolymers of propylene oxide, silicone surfactants (surface active agents containing a silicone backbone), gemini surfactants, polysorbates, fatty acid esters of sorbitan, oxyethylenated fatty esters of sorbitan, ethoxylated fatty ethers, ethoxylated fatty esters, fatty acid esters of sugars, fatty alkyl ethers of sugars, fatty acid esters of glycerol, fatty acid esters of polyglycerol, etc. The emulsifiers can be anionic, cationic or nonionic.

The preferred emulsifiers according to the invention belong to the so called Glyceryl Fatty Acid Esters of the following generic structure:

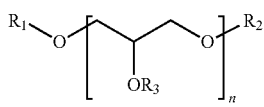

Wherein R represents the residue of a fatty acids or hydrogen and n varies between 1 and 20. Such esters are nonionic and as such having low potential to irritate the skin.

In principle, R can be the residue of any fatty acid, such as for example acetic acid (C2), adipic acid (C6), arachidic acid (C22), arachidonic acid (C20), beeswax fatty acids, behenic acid (C22), capric acid (010), caprylic acid (C8), citric acid (C3), decanoic acid (010), eicosandioic acid (C20), erucic acid (C22), ethylhexanoic acid (C8), heptanoic acid (C7), hydroxystearic acid (C18), isopalmitic acid (C16), isostearic acid (C18), isotridecanoic acid, lactic acid (C3), lanolin acids, lauric acid (C12), linoleic acid (C18), linolenic acid (C18), myristic acid (C14), oleic acid (C18), palmitic acid (C16), palmitoleic acid (C16), pentadecanoic acid (C15), ricinoleic acid (C18), stearic acid (C18), undecylenic acid (C11) and others; this list being non exhaustive. Suitable fatty acids can be saturated, unsaturated, linear or branched. The fatty acids can be obtained from various oils and waxes, for example the vegetable oils or waxes presented previously in the text. Such oils and waxes usually contain a mixture of fatty acids and the fatty acids are referred to collectively by their origin, for example fatty acids derived from hydrogenated rapeseed oil, fatty acids derived from olive oil, hydrogenated mixed long chain acids derived from rosin, the hydrogenated mixed long chain acids derived from soy, the fatty acids derived from montan acid wax, the fatty acids derived from coconut oil, the fatty acids derived from tallow; this list being non exhaustive. Glyceryl esters with fatty acids derived from oils or waxes are often referred to as glyceryl esters of the respective oil or wax (for example apricot kernel oil glyceryl esters, argan oil glyceryl esters, avocado oil glyceryl esters, etc.) and are understood as mixture of glyceryl esters of various fatty acids that are present in the respective oil or wax.

With the reference to the glyceryl fatty acid esters generic structure, in monoglyceryl monoesters, R1 and R3 represent hydrogen, n=1 and R2 is the residue of a fatty acid, preferably one that contains 6 to 22 carbon atoms. A non-exhaustive list of examples of monoglyceryl monoesters with preferred fatty acids follows. Glyceryl adipate (26699-71-8), is the ester of glycerin and adipic acid. Glyceryl arachidate (30208-87-8 or 50906-68-8) is the ester of glycerin and arachidic acid. Glyceryl arachidonate (CAS 129691-05-0 or 35474-99-8) is the ester of glycerin and arachidonic acid. Glyceryl behenate (CAS 6916-74-1, 77538-19-3 OR 30233-64-8) is the ester of glycerin and behenic acid (e.g. trade name Compritol® 888 CG ATO from company Gattefossé). Glyceryl cocoate (CAS 61789-05-7) is the ester of glycerin and coconut fatty acids (e.g. trade name IMWITOR® 928 from company 101 Oleo GmbH). Glyceryl caprate (CAS 11139-88-1, 26402-22-2) is the ester of glycerin and capric acid (e.g. trade name Dermosoft® GMC from company Dr. Straetmans). Glyceryl caprylate (CAS 26402-26-6) is the monoester of glycerin and caprylic acid (e.g. trade name Dermosoft® GMCY from company Dr. Straetmans). Glyceryl erucate (CAS 28063-42-5) is the ester of glycerin and erucic acid. Glyceryl heptanoate (CAS 26402-24-4) is the ester of glycerin and heptanoic acid. Glyceryl hydroxystearate (CAS 1323-42-8) is the ester of glycerin and hydroxystearic acid (e.g. trade name Naturechem® GMHS from company Vertellus Performance Material, Inc). Glyceryl isostearate (CAS 61332-02-3, 66085-00-5) is the ester of glycerin and isostearic acid (e.g. trade name Cithrol™ GMIS 40 from company Croda). Glyceryl laurate (142-18-7, 27215-38-9 and 37318-95-9) is the ester of glycerin and lauric acid (e.g. trade name Monomuls® 90-L 12 from company BASF). Glyceryl linoleate (2277-28-3, 26545-74-4 or 37348-65-5) is the ester of glycerin and linoleic acid. Glyceryl linolenate (18465-99-1 or 56554-41-7) is the ester of glycerin and linolenic acid. Glyceryl Linoleate and Glyceryl Linolenate are available as a mixture under trade name Vitamin F Glyceryl Ester CLR from company CLR Chemisches Laboratorium Dr. Kurt Richter GmbH. Glyceryl myristate (CAS 27214-38-6 or 589-68-4) is the ester of glycerin and myristic acid. Glyceryl oleate (CAS 111-03-5, 161403-66-3, 25496-72-4, 37220-82-9 and 68424-61-3) is the ester of glycerin and oleic acid (e.g. trade name TEGIN® 0 V from company Evonik Industries AG Personal Care). Glyceryl palmitate (CAS 26657-96-5 or 542-44-9) is the ester of glycerin and palmitic acid. Glyceryl stearate (CAS 11099-07-3, 123-94-4, 31566-31-1 or 85666-92-8) is the ester of glycerin and stearic acid (e.g. trade name Cutina® GMS V from company BASF). Glyceryl undecylenate (CAS 123759-97-7 or 62285-15-8) is the ester of glycerin and undecylenic acid.

With the reference to the glyceryl fatty acid esters generic structure, when besides the R2 also R1 or R3 represent a residue of fatty acid and n=1, then the structure represents monoglyceryl diesters. Examples of monoglyceryl diesters include Glyceryl Sesquioleate, Glyceryl palmitate lactate, Glyceryl stearate/acetate, Glyceryl stearate citrate, Glyceryl stearate lactate or Glyceryl stearate succinate. Glyceryl stearate citrate (CAS 55840-13-6 or 91744-36-4) is for example available under trade name AXOL® C 62 Pellets from the company Evonik Industries AG Personal Care.

With the reference to the glyceryl fatty acid esters generic structure, when all three of R1, R2 and R3 represent a residue of fatty acid and n=1 then the structure represents monoglyceryl triesters. Examples of monoglyceryl triesters include glyceryl laurate diacetate, glyceryl stearate diacetate, glyceryl tribehenate/isostearate/eicosandioate or glyceryl tristearate. Glyceryl tribehenate/isostearate/eicosandioate (CAS 922708-02-9) is for example available under the trade name NOMCORT® SG from the company Ikeda Corporation.

With the reference to the glyceryl fatty acid esters generic structure, in polyglyceryl monoesters, R1 and R3 represent hydrogen, n varies from 2 to 20 and R2 is the residue of a fatty acid, preferably one that contains 6 to 22 carbon atoms. When naming polyglyceryl esters, the number of repeating units of the polyglyceryl moiety (n) is usually stated as "-n" that follows the word "polyglyceryl", for example polyglyceryl-3, polyglyceryl-4, polyglyceryl-6 etc. It is understood, that in polyglyceryl esters n represents the average number of repeating units. A non-exhaustive list of examples of polyglyceryl monoesters with preferred fatty acids follows. Capric acid polyglyceryl monoesters with n=2, 3, 4, 5, 6 or 10, for example polyglyceryl-2 caprate (CAS 156153-06-9/ e.g. Dermosoft® DGMC from Dr. Straetmans), polyglyceryl-3 caprate (CAS 133654-02-1, 51033-30-8 or 74504-65-7/e.g. TEGOSOFT® PC 31 from Evonik Industries AG Personal Care) or polyglyceryl-4 caprate (CAS 160391-93-5, 74504-65-7/e.g. TEGOSOFT® PC 41 from Evonik Industries AG Personal Care). Caprylic acid polyglyceryl monoesters with n=2, 3, 4, 6 or 10, for example Polyglyceryl-3 Caprylate (CAS 108777-93-1/e.g. TEGO® Cosmo P 813 from Evonik Industries AG Personal Care) or Polyglyceryl-10 Caprylate (CAS 51033-41-1). Isostearic acid polyglyceryl monoesters with n=2, 3, 4, 5, 6 or 10, for example Polyglyceryl-2 isostearate (CAS 73296-86-3 or 81752-33-2), Polyglyceryl-3 isostearate (CAS 127512-63-4), Polyglyceryl-4 Isostearate (CAS 63705-03-3 or 91824-88-3/e.g. ISOLAN® GI 34 from Evonik Industries AG Personal Care), Polyglyceryl-6 Isostearate (CAS 126928-07-2), Polyglyceryl-10 Isostearate (CAS 133738-23-5). Lauric acid polyglyceryl monoesters with n=2, 3, 4, 5, 6 or 10, for example Polyglyceryl-2 Laurate (CAS 96499-68-2), Polyglyceryl-3 Laurate (CAS 51033-31-9), Polyglyceryl-4 Laurate (CAS 74504-64-6 or 75798-42-4/e.g. TEGO® Care PL 4 from Evonik Industries AG Personal Care), Polyglyceryl-5 Laurate (CAS 128738-83-O/e.g. Dermofeel® G 5 L from Dr. Straetmans), Polyglyceryl-6 Laurate (CAS 51033-38-6/e.g. PGLLA 106KC from KCl Limited) or Polyglyceryl-10 Laurate (CAS 34406-66-1/e.g. Dermofeel® G 10 L from Dr. Straetmans). Oleic acid polyglyceryl monoesters with n=2, 3, 4, 5, 6, 8 or 10, for example Polyglyceryl-2 Oleate (49553-76-6/e.g. Polyglyceryl-2 Oleate), Polyglyceryl-3 Oleate (33940-98-6/e.g. ISOLAN® GO 33 from Evonik Industries AG Personal Care), Polyglyceryl-4 Oleate (71012-10-7), Polyglyceryl-5 Oleate (86529-98-8/e.g. Dermofeel® G 5 O from Dr. Straetmans), Polyglyceryl-6 Oleate (79665-92-2), Polyglyceryl-8 Oleate (75719-56-1) or Polyglyceryl-10 Oleate (79665-93-3/e.g. Polyaldo® 10-1-O KFG from Lonza). Polyglyceryl oleate esters are also referred to by a generic CAS Number 9007-48-1. Stearic acid polyglyceryl monoesters with n=2, 3, 4, 5, 6, 8 or 10, for example Polyglyceryl-2 Stearate (CAS 12694-22-3/e.g. Hostacerin® DGMS from Clariant International Ltd.), Polyglyceryl-3 Stearate (26855-43-6 or 27321-72-8/e.g. Dermofeel® PS from Dr. Straetmans), Polyglyceryl-4 Stearate (CAS 26855-44-7 or 68004-11-5), Polyglyceryl-6 Stearate (CAS 95461-65-7), Polyglyceryl-8 Stearate (CAS 75719-57-2) or Polyglyceryl-10 Stearate (CAS 79777-30-3).

With the reference to the glyceryl fatty acid esters generic structure, in polyglyceryl diesters, R3 represents hydrogen, n varies from 2 to 20 and R1 and R2 are the residue of a fatty acid, preferably one that contains 6 to 22 carbon atoms. A non-exhaustive list of examples of polyglyceryl monoesters with preferred fatty acids follows. Polyglyceryl-3 Dicaprate, Polyglyceryl-6 Dicaprate, Polyglyceryl-5 Dicaprylate (108777-93-1), Polyglyceryl-3 Dicocoate, Polyglyceryl-10 Dicocoate, Polyglyceryl-10 Didecanoate (182015-59-4), Polyglyceryl-2 Diisostearate (63705-03-3 or 67938-21-O/ e.g. Dermol DGDIS from ALZO International Inc.), Polyglyceryl-3 Diisostearate (63705-03-3 or 66082-42-6/ e.g. Lameform® TGI from BASF), Polyglyceryl-6 Diisostearate, Polyglyceryl-10 Diisostearate (102033-55-6 or 63705-03-3), Polyglyceryl-15 Diisostearate, Polyglyceryl-4 Dilaurate, Polyglyceryl-5 Dilaurate, Polyglyceryl-10 Dilaurate, Polyglyceryl-10 Dimyristate, Polyglyceryl-2 Dioleate (60219-68-3 or 67965-56-4), Polyglyceryl-3 Dioleate (79665-94-49/e.g. Plurol® Oleique CC 497 CG from Gattefossé), Polyglyceryl-5 Dioleate (Dermofeel® G5DO from Dr. Straetmans), Polyglyceryl-6 Dioleate (76009-37-5), Polyglyceryl-10 Dioleate (33940-99-7/e.g. SALACOS® PG-218 from Ikeda Corporation), Polyglyceryl-6 Dipalmitate, Polyglyceryl-10 Dipalmitate (e.g. Polyaldo® 10-2-P from Lonza), Polyglyceryl-2 Distearate (9009-32-9), Polyglyceryl-4 Distearate, Polyglyceryl-6 Distearate (34424-97-0/e.g. Plurol® Stearique WL 1009 from Gattefossé) or Polyglyceryl-10 Distearate (12764-60-2).

With the reference to the glyceryl fatty acid esters generic structure, in polyglyceryl multiesters, n varies from 2 to 20 and R1 and R2 and R3 are the residue of a fatty acid, preferably one that contains 6 to 22 carbon atoms, however in a given molecule all of R1, R2 and R3 may represent fatty acid or some of R1, R2 or R3 may represent hydrogen. In the latter case, the total number of fatty acid residues per molecule will be less that the total number of R (R1+R2+R3) available. A non-exhaustive list of examples of polyglyceryl multiesters with preferred fatty acids follows. Polyglyceryl-10 Decaethylhexanoate, Polyglyceryl-10 Decahydroxystearate, Polyglyceryl-10 Decaisostearate, Polyglyceryl-10 Decalinoleate (CAS 68900-96-9), Polyglyceryl-10 Decamacadamiate, Polyglyceryl-10 Decaoleate (CAS 11094-60-3/ e.g. Polyaldo™ DGDO KFG from Lonza), Polyglyceryl-10 Decastearate (CAS 39529-26-5), Polyglyceryl-10 Dodecabehenate, Polyglyceryl-10 Dodecacaprate, Polyglyceryl-10 Dodecacaprylate, Polyglyceryl-6 Heptacaprylate, Polyglyceryl-20 Heptacaprylate, Polyglyceryl-10 Heptahydroxystearate (CAS 103175-09-3), Polyglyceryl-10 Heptastearate (CAS 99126-54-2), Polyglyceryl-20 Hexacaprylate, Polyglyceryl-10 Hexaerucate, Polyglyceryl-10 Hexaisostearate, Polyglyceryl-6 Hexaoleate (CAS 95482-05-6), Polyglyceryl-10 Hexaoleate (CAS 65573-03-79/contained in the product PELEMOL® P-1263 from Phoenix Chemical, Inc.), Polyglyceryl-5 Hexastearate, Polyglyceryl-6 Hexastearate, Polyglyceryl-10 Nonaerucate (CAS 155808-79-0), Polyglyceryl-10 Nonaisostearate, Polyglyceryl-6 Octacaprylate (e.g. SALACOS HG-8 from Nisshin Oillio Group, Ltd.), Polyglyceryl-20 Octaisononanoate, Polyglyceryl-6 Octastearate, Polyglyceryl-6 Pentacaprylate, Polyglyceryl-10 Pentacaprylate, Polyglyceryl-10 Pentahydroxystearate, Polyglyceryl-10 Pentaisostearate, Polyglyceryl-10 Pentalaurate, Polyglyceryl-10 Pentalinoleate, Polyglyceryl-5 Pentamyristate, Polyglyceryl-4 Pentaoleate (CAS 103230-29-1), Polyglyceryl-6 Pentaoleate (CAS 104934-17-0), Polyglyceryl-10 Pentaoleate (CAS 86637-84-5), Polyglyceryl-3 Pentaolivate, Polyglyceryl-4 Pentapalmitate, Polyglyceryl-3 Pentaricinoleate, Polyglyceryl-6 Pentaricinoleate, Polyglyceryl-10 Pentaricinoleate, Polyglyceryl-4 Pentastearate (CAS 99570-00-0), Polyglyceryl-6 Pentastearate (CAS 99734-30-2), Polyglyceryl-10 Pentastearate (CAS 95461-64-6), Polyglyceryl-6 Sesquicaprylate (CAS 108777-93-1, 946492-22-4, 946492-23-5), Polyglyceryl-2 Sesquiisostearate (e.g. Hostacerin® DGI from Clariant International Ltd.), Polyglyceryl-6 Sesquiisostearate, Polyglyceryl-2 Sesquioleate (e.g. Dermofeel® GO soft from Dr. Straetmans), Polyglyceryl-2 Sesquistearate (CAS 9009-32-9), Polyglyceryl-6 Sesquistearate (CAS 112939-69-2), Polyglyceryl-10 Sesquistearate, Polyglyceryl-6 Tetrabehenate, Polyglyceryl-6 Tetracaprylate, Polyglyceryl-10 Tetradecanedioate, Polyglyceryl-2 Tetraisostearate (CAS 121440-30-0), Polyglyceryl-10 Tetralaurate, Polyglyceryl-2 Tetraoleate, Polyglyceryl-10 Tetraoleate (CAS 34424-98-1), Polyglyceryl-2 Tetrastearate (CAS 72347-89-8), Polyglyceryl-5 Tribehenate, Polyglyceryl-6 Tricaprylate, Polyglyceryl-10 Tricocoate, Polyglyceryl-10 Tridecanoate (CAS 217782-56-4), Polyglyceryl-10 Trierucate, Polyglyceryl-2 Triisostearate (CAS 120486-24-0), Polyglyceryl-3 Triisostearate (CAS 66082-43-7), Polyglyceryl-5 Triisostearate, Polyglyceryl-10 Triisostearate, Polyglyceryl-10 Trilaurate (e.g. PGLLA 310KC from KCl Limited), Polyglyceryl-5 Trimyristate, Polyglyceryl-5 Trioleate, Polyglyceryl-10 Trioleate (CAS 102051-00-3), Polyglyceryl-3 Triolivate, Polyglyceryl-4 Tristearate (CAS 99734-29-9), Polyglyceryl-5 Tristearate (CAS 9009-32-9).

Advantageously, a mixture of two or more glyceryl or polyglyceryl esters can be used. In some cases, glyceryl or polyglyceryl esters are only available as a mixture because the particular fatty acids used for glycerol or polyglycerol esterification themselves are only available as a mixture. This is for example the case with glyceryl cocoates since the fatty acids of coconut oil varieties may be a mixture of caprylic, decanoic, lauric, myristic, palmitic, oleic and other fatty acids. In other cases, the mixing is deliberate.

According to the invention, the amount of emulsifier is between 5% w/w and 30% w/w of the total weight of W/O microemulsion. In another embodiment, the amount of emulsifier is preferably between 7% w/w and 25% w/w of the total weight of W/O microemulsion. In another embodiment, the amount of emulsifier is preferably between 9% w/w and 20% w/w of the total weight of the W/O microemulsion.

In another embodiment, the cosmetic W/O microemulsion as recited in one of claims 1 through 7, characterized in that the fatty acid ester(s) of glycerol or fatty acid ester(s) of polyglycerol are selected from monoglyceryl monoesters, monoglyceryl diesters, monoglyceryl triesters, polyglyceryl monoesters, polyglyceryl diesters or polyglyceryl multiesters. These ingredients are particularly suitable to achieve the advantages described herein.

In another embodiment, the cosmetic W/O microemulsion as recited in one of claims 1 through 8, characterized in that the W/O microemulsion comprises at least two different fatty acid ester(s) of glycerol and/or fatty acid ester(s) of polyglycerol. The use of two different fatty acid ester(s) of glycerol and/or fatty acid ester(s) of polyglycerol enables the development of the emulsifier system, for example using the HLP method or PIT method, which most optimally fits the given W/O microemulsion system.

In another embodiment, the cosmetic W/O microemulsion as recited in one of claims 1 through 9, characterized in that the fatty acid ester(s) of glycerol or fatty acid ester(s) of polyglycerol are selected from polyglyceryl monoesters, polyglyceryl diesters or polyglyceryl multiesters with 5 repeating glycerol moieties. The fatty acid ester(s) of glycerol or fatty acid ester(s) of polyglycerol with 5 repeating glycerol moieties have are particularly suitable to achieve the advantages described herein and also possess good consumer skin tolerance. The W/O microemulsion according to the invention comprises an aqueous phase. The aqueous phase can be made entirely of water. In principle, various water qualities are suitable such as municipal tap water, softened water, deionized water, water purified by reverse osmosis, distilled water, double-distilled water, water for injection as defined in Pharmacopoeia, etc. Advantageously, the water should be sufficiently free from contaminants, including microorganisms, that may have a negative effect of the W/O microemulsion or on the user of the W/O microemulsion. The aqueous phase can also be a uniformly distributed mixture of water and substances which are water-soluble or mixable with water.

The amount of water in the W/O microemulsion is very important for good dispensability and the amount of water according to the invention does not exceed 20% w/w of the total weight of W/O microemulsion. According to the invention, the amount of water is between 5% w/w and 20% w/w of the total weight of W/O microemulsion. In another embodiment, the amount of water is preferably between 6% w/w and 15% w/w of the total weight of W/O microemulsion. In another embodiment, the amount of water is preferably between 7% w/w and 13% w/w of the total weight of W/O microemulsion.

In another embodiment, the cosmetic W/O microemulsion as recited in one of claims 1 through 10 is characterized in that the W/O microemulsion comprises water in the amounts between 6% w/w and 15% w/w, particularly between 7% w/w and 13% w/w.

An important parameter of the W/O microemulsion according to the invention is the ratio of the amount of water to the amount of the emulsifier in the W/O microemulsion. Crucially, the ratio of water to the emulsifier is of especial importance, which is not the same as the ratio of aqueous phase to the emulsifier, since the aqueous phase can comprise water soluble ingredients in addition to water. According to the invention, the ratio between the amount of water as weight % of the total weight of W/O microemulsion and the amount of the emulsifier as weight % of the total weight of W/O microemulsion ranges from 4:1 to 2:3. In another embodiment, the ratio between the amount of water as weight % of the total weight of W/O microemulsion and the amount of the emulsifier as weight % of the total weight of W/O microemulsion preferably ranges from 2:1 to 1:1.9. In another embodiment, ratio between the amount of water as weight % of the total weight of W/O microemulsion and the amount of the emulsifier as weight % of the total weight of W/O microemulsion preferably ranges from 1:1 to 1:1.8. In another embodiment, the ratio between the amount of water as weight % of the total weight of W/O microemulsion and the amount of the emulsifier as weight % of the total weight of W/O microemulsion preferably ranges from 1:1.2 to 1:1.6.

In another embodiment, the cosmetic W/O microemulsion as recited in one of claims 1 through 11, is characterized in that the ratio between the amount of water as weight % relative to the total weight of W/O microemulsion and the amount of the emulsifier as weight relative to the total weight of W/O microemulsion ranges from 4:1 to 2:3, preferably ranges from 2:1 to 1:1.9, even more preferably ranges 1:1 to 1:1.8, particularly ranges from 1:1.2 to 1:1.6.

The W/O microemulsion according to the invention comprises at least one polyol as a co-surfactant. A polyol is an alcohol containing multiple hydroxyl groups (—OH functional groups). Polyols comprising two hydroxyl groups are also referred to as diols. Polyols comprising three hydroxyl groups are also referred to as triols. Suitable polyol co-surfactants can be selected from polyols comprising a linear or branched carbon backbone of 2 to 6 carbon atoms and comprising primary hydroxyl groups, secondary hydroxyl groups or a mixture of primary and secondary hydroxyl groups.

Suitable diol co-surfactants include for example 1,10-decanediol, 1,2-butanediol, 1,2-hexanediol, 1,4-butanediol (CAS 110-63-4), 1,5-pentanediol (CAS 111-29-5), 2,3-butanediol (CAS 513-85-9), hexanediol (CAS 629-11-8), ethyl hexanediol (94-96-2), isopentyldiol, methylpropanediol, propanediol, etc.; this list being non-exhaustive. 1,2-hexanediol (CAS 6920-22-5) is available for example under trade name Hexiol from company Minasolve. Isopentyldiol (CAS 50468-22-9/2568-33-4) is available for example under trade name ISOPENTYLDIOL from company Kuraray Europe GmbH. Methylpropanediol (CAS 2163-42-0) is available for example under trade name DUB DIOL from company SEPPIC. Propanediol (504-63-2/26264-14-2) is available under trade name Activonol-3 from company ActivON. Co. Ltd.

Diols in which the two hydroxyl groups are attached to different carbon atoms are also commonly referred to as glycols. Suitable diol co-surfactants which are commonly referred to as glycols include for example butylene glycol (butylene glycol is a term which can be applied to any of the stereoisomers 1,2-butanediol, 1,3-butanediol, 1,4-butanediol or 2,3-butanediol), dipropylene glycol (110-98-5/ 25265-71-8), glycol (107-21-1), hexylene glycol, neopentyl glycol (126-30-7), pentylene glycol, propylene glycol, etc.; this list being non-exhaustive.

Butylene glycol (107-88-0) is available for example under trade name Centella Herb (Gotu Kola) Floraceutical® from the company Bio-Botanica, Inc. Butylene glycol, a term which can be applied to any of the stereoisomers 1,2-butanediol, 1,3-butanediol, 1,4-butanediol or 2,3-butanediol. Hexylene glycol (CAS 107-41-5) is available for example under trade name Hexylene Glycol from the company Solvay Novecare. Pentylene glycol (5343-92-0) is available for example under trade name Activonol-5 from the company ActivON. Co. Ltd. Suitable triol co-surfactants include for example glycerol (glycerin) or 1,2,6-hexanetriol (CAS 106-69-4)

Suitable polyols with more than three hydroxyl groups include erythritol (CAS 7541-59-5; 149-32-6), threitol (CAS 2418-52-2/7493-90-5), xylitol (CAS 87-99-0), mannitol (CAS 69-65-8), sorbitol (CAS 50-70-4), etc.; this list being non-exhaustive. Erythritol is available for example under trade name ERYLITE® from company Jungbunzlauer International AG.

Advantageously, the W/O microemulsion comprises a co-surfactant glycerin or propylene glycol. Advantageously, a mixture of glycerin and propylene glycol can be used. Glycerin (56-81-5) is for example available under trade name Dermorganics® Glycerin from the company Dr. Straetmans. Propylene glycol or Propanediol (CAS 57-55-6) is for example available under the trade name Zemea® USP-FCC Propanediol from the company DuPont Tate & Lyle BioProducts. Besides playing role in formation and stabilization of the W/O microemulsion, co-surfactant is suitable to assist with incorporation of cosmetic ingredients to the W/O microemulsion, such as active compounds or preservatives. The W/O microemulsion according to the invention comprises 0.2-15% w/w co-surfactant. In another embodiment, the W/O microemulsion according to the invention comprises preferably 0.5-12% w/w co-surfactant and even more preferably 1-10% co-surfactant.

The W/O microemulsion may optionally comprise short chain alcohol as a co-solvent. Besides playing role in formation and stabilization of the W/O microemulsion, co-solvents are suitable to assist with incorporation of cosmetic ingredients to the W/O microemulsion, such as active compounds or preservatives. In addition, co-solvents can be used to increase the clarity of the W/O microemulsion. Suitable short chain alcohols co-solvents can be selected from C2 to C6 branched or straight chains alcohols, such as ethanol, 1-propanol (n-Propanol), 2-propanol (iso-propanol), hexanol, etc. Preferred co-solvents are ethanol, 2-propanol and n-propanol. A mixture of two or more co-solvents is advantageous. Advantageously, a mixture of ethanol and 2-propanol can be used. In another embodiment, the W/O microemulsion comprises 0.1-10% w/w co-solvent, preferably 0.5-7% co-solvent even more preferably 0.8-5% co-solvent. In another embodiment, the co-solvent is absent.

The W/O microemulsion according to the invention is surprisingly exhibits high degree of formulation stability when incorporating additional ingredients with varied hydrophilic-lipophilic balance (HLB) values for as long as the amount and the spreading value of the oil phase ingredients remains within described range and the amount of water does not exceed the described upper limit amounts. The W/O microemulsion according to the invention can optionally comprise the following skin care ingredients: emollients, occlusive, moisturizers, humectants, lipid layer enhancer and other skin care ingredients. An emollient (from Latin emollient-meaning 'making soft') is any cosmetic substance that can soften the skin after being externally applied to it. For the purposes of the present invention an emollient is preferably a skin care substance which is composed predominantly of linear, saturated hydrocarbon backbone which may contain few of the following chemical structure elements: brunched chains, saturated hydrocarbon rings as well as C=C, C—O, C=O, and O—H bonds. An occlusive is any skin care substance that is applied externally to create a film over the skin which reduces the rate of water loss from the skin surface. In doing so, occlusives help maintain the skin moisturization in medium to long term and help generating a prolonged positive after-feel. Known occlusives are for example propylene glycol, silicon compounds such as dimethicone, squalane (of animal or plant origin), lanolin, mineral oils, allantoin, cocoa butter, waxes, etc. A moisturizer is a skin care substance that increases the hydration (water content) of upper layer of the skin. Humectants are skin care substances that have the ability to reversibly bind water and thus help retain water in skin. The humectant can not only retain water in the skin but also draw water to the skin. Humectants possess hydrophilic groups that are able to form hydrogen bonds with water molecules, such as —NH3 (amines group), —COOH group (carboxylic group) or —OH (hydroxyl group). Known humectants are for example glycerin, sorbitol, butylene, sugars and sugar derivatives, proteins, peptides, oligopeptides, amino acids, amino acids derivatives, etc. It will be known to the cosmetic chemist, that skin care substances often have several functions. For example, a humectant may have moisturizing and emollient properties, etc.

The W/O microemulsion according to the invention can optionally comprise auxiliary substances, such as preservatives, bactericides, fungicides, substances for preventing foaming, dyes and colorants, chelating agents, foam stabilizers, mineral salts, silicone derivatives, buffers, pH regulators, propellant gases, etc., provided the addition of these substances does not negatively affect the dispensability.

In another embodiment, the cosmetic W/O microemulsion as recited in claims 1 through 13 is characterized in that the W/O microemulsion comprises at least one of emollients, occlusives, moisturizers, humectants, lipid layer enhancers, cosmetic auxiliary ingredients or cosmetic active ingredients.

The W/O microemulsion according to the invention can optionally comprise active ingredients such as for example anti-aging, anti-cellulite, anti-acne, anti-rosacea, anti-neurodermatitis and similar ingredients. Advantageously, the W/O microemulsion comprises an extract of plant material. Advantageously, the W/O microemulsion comprises a water-soluble extract of plant material. Advantageously, the W/O microemulsion comprises a water-miscible extract of plant material.

In another embodiment, the cosmetic W/O microemulsion as recited in claims 1 through 12 is characterized in that the W/O microemulsion comprises at least one water-soluble extract of plant material.

In another embodiment, the amount of water-soluble plant material is between 1-20%, preferably 3 and 18% and even more preferably between 5 and 15%.

The choice of the ingredients in the preparation of the W/O microemulsion according to the invention is preferably driven by optimizing the aesthetic and sensory parameters of the W/O microemulsion. Preferably ingredients without a sticky, tacky, greasy or oily feeling on the skin are chosen or the amount of ingredient with sticky, tacky, greasy or oily feeling on the skin is limited so that no such sticky, tacky, greasy or oily feeling is perceived after application on the skin.

The preparations according to the invention are stable for at least 8 months at 50° C. and for at least 12 months at room temperature.

The W/O microemulsion according to the invention is preferably transparent. The degree of light transparency of a W/O microemulsion can be measured using a spectrophotometer, such as the DU 530 Life Science UV/Vis Spectrophotometer manufactured by Beckman Coulter. For measurement, two ml of the W/O microemulsion are pipetted into cuvettes with the light path of 1 cm and the light transmittance at 600 nm is measured. Sufficiently transparent W/O microemulsion will have transmittance values above 85%, with preferable values above 90% and ideal values above 95%.

The W/O microemulsion according to the invention have preferably globules with average size below 350 nm. To determine the average size of the aqueous phase globules in the W/O microemulsion can be measured by light scattering. For light scattering measurements, a dynamic light scattering spectrometer, such as an ALV-NIBS High Performance Particle Sizer equipped with He-Ne Laser with about 3 mW output power at 633 nm, digital correlator ALV-5000 and a single photon detector module, manufactured by ALV-mbH in Langen/Germany can be used. Aqueous phase globules with sufficiently small globules will contain globules with average size below 350 nm, the preferable average size being 250 nm and the ideal average size being below 150 nm.

A skilled cosmetic chemist will have no difficulty to identify the INCI names of the compounds mentioned, e.g. by searching the EU Cosmetic ingredient database using the compound name or CAS number.

To manufacture the W/O microemulsion of the invention, first all ingredients of the oil phase are blended together. In a separate vessel, water is mixed with the co-surfactant and co-solvent (when present). If the emulsifier is predominantly hydrophilic, it can be introduced into the aqueous phase; if the emulsifier is predominantly lipophilic, it can be introduced into the oil phase. However, it is also understood that the emulsifiers particularly suitable for the W/O microemulsions according to the invention are neither well soluble in the aqueous nor in oil phase and will preferentially accumulate at the contact point of aqueous/oil phase. In this case, a fine suspension of the emulsifier in the respective phase must be created. To assist with emulsifier dispersion, the respective phase may be heated up to 80° C. Once the emulsifier is sufficiently dispersed, then the oil and aqueous phases are combined and thoroughly mixed to create the W/O microemulsion. The W/O microemulsion is then allowed to cool to under 40° C. before incorporating further ingredients under gentle mixing.

Except in the operating and comparative examples, or where otherwise explicitly indicated, all numbers in this description indicating amounts or ratios of materials or physical properties of materials are to be understood as modified by the word "about". When used, the term "comprising" is intended to include the presence of stated ingredients or components, but not meant to preclude the presence or addition of one or more additional ingredients or components. Unless indicated otherwise, all percentages are intended to be percentages by weight. The numerical values refer to the weight fractions with regard to the total mass of the preparation, unless stated otherwise. The definitions provided here are provided to better illustrate the invention and are not meant as a restriction. In the case of restrictions to preferentially mentioned substances, then their preferred weight fractions ranges also refer to the constituents then selected. The other constituents excluded by the restriction then are no longer added to the listed fraction ranges.

The FIG. 1 shows a cross-section through the device to test the dispensability of the microemulsion.

Referring to the FIG. 1, the testing device is comprised of a pump (1), having a pump housing (2), a pumping mechanism (3), a pump inlet (4) and a pump outlet (5). The pumping mechanism (3) is capable of pumping at a rates from 30 microliters per minute to 20 milliliters per minute. The pumping mechanism (3) is connected to the pump inlet (4) and pump outlet (5) and is capable of unidirectional pumping (forcible transfer) of liquids from the pump inlet (4) towards pump outlet (5) under expenditure of energy, such as electrical energy. The pump housing (2) contains a programmable controller (6) to regulate, control and keep constant the speed of the pumping mechanism (3) thereby regulating, controlling and keeping constant the rate of liquid flowing through the pump outlet. In particular, the controller (6) is able to keep the flow rate at +/−2% of the predefined value. An inlet tube (7) is connected with one of its ends to the pump inlet (4) whereas the other end of the inlet tube (7) is free and is positioned within the liquid container (11). The inlet tube (7) serves for the aspiration of the liquid (microemulsion to be tested (12)) from the liquid container (11) and for the liquid transfer from the liquid container (11) via the pump inlet (4) to the pumping mechanism (3). An outlet tube (8) is connected with one of it ends to the pump outlet (5) and is connected with another end to the nozzle pipe (9). The outlet tube (8) serves for transfer of the liquid from pumping mechanism (3) via the pump outlet (5) to the to the nozzle pipe (9). The inner diameter of the inlet tube (7), outlet tube (8), pump inlet (4) and pump outlet (5) can vary from 1.5 mm to 9.0 mm. The nozzle pipe (9) is connected with one end to the outlet tube (8) whereas the other end is positioned to hung free and forms the nozzle pipe orifice (10). The nozzle pipe (9) is made from polyethylene and has a length (L) equal to 15 mm and contains a round inner channel. The wall thickness of the nozzle pipe (9) can vary from 0.5 to 3 mm. The inner diameter (D) of the nozzle pipe (9) (diameter of the round inner channel) is equal to 2 mm and is constant through the length (L) of the nozzle pipe (9) and the nozzle pipe orifice (10) has the same inner diameter (D) as the nozzle pipe (9). During the test, the nozzle pipe (9) is positioned vertically in such a way that when the detached drops (14) leave the nozzle pipe orifice (10), the detached drops (14) fall along the imaginary line which runs along the length of nozzle pipe and passes through the center of the nozzle pipe orifice (10). The inlet tube (7), the outlet tube (8) and the nozzle pipe (9) are preferably made from transparent material in order to control the absence of bubbles in the liquid that being pumped through them. Suitable pump (1) is for example Eldex® Optos Piston Metering Pump, ¼" stainless head, 0.02 to 40 mL/min range, 1500 psi available from the company Cole-Palmer under catalog number EW-73150-50. Cole-Palmer also sells tubing suitable as the inlet tube (7) and the outlet tube (8). The nozzle pipe (9) can be made by cutting a 15 mm piece from a polyethylene tube manufactured by the company DEUTSCH & NEUMANN that has an inner diameter (D) of 2.00 mm, outer diameter of 4.00 mm, wall thickness of 1.00 mm and is available from the company VWR international under the catalog number DENE3550204.

The testing is carried out ambient conditions, meaning in a room or enclosure with temperature of 22±2° C. and atmospheric pressure between 980-1040 h Pa. All parts of the testing device and the microemulsion to be tested must be conditioned to the ambient temperature before the test and care must be taken that during the operation the temperature of the microemulsion does not decrease below 20° C. or does increase above 24° C. For the testing, the liquid container (11) is filled with the microemulsion to be tested (12) to such a degree, that the free end of the inlet tube (7) remains immersed in the microemulsion for entire duration of the test. The microemulsion to be tested (12) is then left to stand in the liquid container (11) until all air bubbles that may have be trapped in the liquid during pouring of the microemulsion to the liquid container (11) have risen to the surface and dissipated. The pump is then operated until the inlet tube (7), the pumping mechanism (3) the outlet tube (8) and the nozzle pipe (9) are completely filled with microemulsion and do not contain air bubbles. The pumping rate is then set to 0.05 milliliters per second or 3.00 milliliters per minute via the programmable controller (6) of the pump. As the microemulsion is pumped through the nozzle pipe emerges from the nozzle pipe orifice (10) it will initially form a pending (hanging) drop (13) since initially, the weight of the drop is not sufficient to overcome the cohesive and adhesive forces within the microemulsion and possibly also the adhesive forces between the microemulsion and the nozzle pipe material. As however more and more of microemulsion exits the nozzle pipe orifice (10) the weight of the hanging drop becomes big enough for the influence of gravity to overcome the cohesive and adhesive forces and detach a drop (14) from the bulk of the microemulsion. The height of the pending drop is therefore a measure of the strength of the plurality of the cohesive and adhesive forces within the microemulsion and possibly of the adhesive forces between the microemulsion and surrounding materials. In addition, the pending drop behavior is a measure of the visco-elastic properties of the liquid.

Using the testing device described, the test begins 30-60 seconds after the pumping rate is constant at 0.05 milliliters per second or 3.00 milliliters per minute (time 0) and lasts 180 seconds. The operation of the device for 30-60 seconds prior to commencing the test is necessary to achieve a flow equilibrium, after which the flow is considered constant. Advantageously, the duration of the test is monitored by a countdown timer. For the entire duration of the test, the operator monitors the height (H) of the pending drops (13) which hang from the nozzle before being detached (atomized) and fall as detached droplet (14). This can be done for example by positioning a graduated ruler (15) close to the nozzle pipe orifice (9) but in such way as not to interfere with the pending drop formation. Advantageously, the formation of the pending drop can be filmed using a video camera and the evaluation to take place by analyzing the produced video recording. In that case, advantageously the pending drop, the ruler and the output of the countdown timer are visible within the same frame of the video recording.

The W/O microemulsions according to the invention are illustrated below in the examples. The examples are intended to further illustrate the invention and are not intended to limit the invention in any way.

EXAMPLE 1. WATER-IN-OIL MICROEMULSION ACCORDING TO THE INVENTION

| Spreading value | Ingredient | % w/w |
|---|---|---|
| Very high | Undecane | 18.69 |
| Very high | Tridecane | 8.01 |
| High | Dibutyl Adipate | 17.00 |
| High | Isopropyl myristate | 5.00 |
| Medium | Decyl Oleate | 5.00 |
| Low | *Helianthus Annuus* Seed Oil | 4.30 |
| | Polyglyceryl-5 Dioleate | 9.50 |
| | Polyglyceryl-5 Oleate | 9.50 |
| | Polyglyceryl-5 Trioleate | 0.25 |
| | Water | 12.40 |
| | Glycerin | 5.00 |
| | Ethanol Denat. | 3.00 |
| | *Leontopodium alpinum* Extract | 1.00 |
| | Ethyl Ferulate | 0.25 |
| | Disodium Uridine Phosphate | 0.05 |
| | *Rosemarinus Officinalis* Leaf Extract | 0.05 |
| | Tocopherol | 0.05 |
| | Parfum | 0.80 |
| | Citric Acid | 0.10 |
| | Potassium Sorbate | 0.035 |
| | Sodium Benzoate | 0.015 |

EXAMPLE 2. WATER-IN-OIL MICROEMULSION ACCORDING TO THE INVENTION

| Spreading value | Ingredient | % w/w |
|---|---|---|
| Very high | Undecane | 17.57 |
| Very high | Tridecane | 7.53 |
| High | Dibutyl Adipate | 17.00 |
| High | Isopropyl myristate | 5.00 |
| Medium | Decyl Oleate | 5.00 |
| Medium | Octyldodecanol | 3.25 |
| Low | *Echium Plantagineum* Seed Oil | 0.50 |
| | Polyglyceryl-5 Dioleate | 9.50 |
| | Polyglyceryl-5 Oleate | 9.50 |
| | Water | 13.00 |
| | Glycerin | 5.50 |
| | Ethanol denat. | 3.00 |
| | 2-propanol | 1.00 |
| | *Peucedanum Ostruthium* Leaf Extract | 0.50 |
| | *Cardiospermum Halicacabum* Flower/Leaf/Vine Extract | 0.50 |
| | Tocopherol | 0.50 |
| | *Helianthus Annuus* (Sunflower) Seed Oil Unsaponifiables | 0.25 |
| | Parfum | 0.80 |
| | Citric Acid | 0.10 |
| | Potassium Sorbate | 0.03 |
| | Sodium Benzoate | 0.02 |

EXAMPLE 3. WATER-IN-OIL MICROEMULSION ACCORDING TO THE INVENTION

| Spreading value | Ingredient | % w/w |
|---|---|---|
| Very high | Undecane | 20.09 |
| Very high | Tridecane | 8.61 |
| High | Dibutyl Adipate | 17.00 |
| High | Isopropyl myristate | 5.00 |
| Medium | Decyl Oleate | 5.00 |
| | Polyglyceryl-5 Dioleate | 9.50 |
| | Polyglyceryl-5 Oleate | 9.50 |
| | Water | 12.40 |
| | Glycerin | 5.50 |
| | Propylene glycol | 2.65 |
| | Ethanol denat. | 3.00 |
| | *Marrubium Vulgare* Extract | 0.50 |
| | *Polypodium Vulgare* Rhizome Extract | 0.25 |
| | *Cetraria Islandica* Thallus Extract | 0.05 |
| | *Sphagnum Magellanicum* Extract | 0.05 |
| | Parfum | 0.80 |
| | Citric Acid | 0.10 |
| | Potassium Sorbate | 0.03 |
| | Sodium Benzoate | 0.02 |

COMPARATIVE EXAMPLES OF WATER-IN-OIL MICROEMULSIONS WITH POOR DISPENSABILITY PROPERTIES

| Spreading value | Ingredient | Example 4 % w/w | Example 5 % w/w | Example 6 % w/w | Example 7 % w/w |
|---|---|---|---|---|---|
| Very high | Undecane | 11.9 | 11.9 | 8.9 | 3.5 |
| Very high | Tridecane | 5.1 | 5.1 | 3.8 | 1.5 |
| High | Dibutyl adipate | 17 | 17 | 12.8 | 5 |
| High | Isoamyl laurate | 17 | | 12.8 | 5 |
| High | Isopropyl myristate | | 17 | | 36 |
| Medium | Decyl oleate | 5 | 5 | 5 | 5 |
| | Polyglyceryl-10 Diisostearate | 10 | 10 | 10 | 10 |
| | Polyglyceryl-5 Oleate | 10 | 10 | 10 | 10 |
| | Water | 15 | 15 | 15 | 15 |
| | Glycerin | 7.5 | 7.5 | 7.5 | 7.5 |
| | *Leontopodium alpinum* Extract | 1.0 | 1.0 | 1.0 | 1.0 |
| | Auxiliaries, preservatives | 0.5 | 0.5 | 0.5 | 0.5 |

LIST OF REFERENCE NUMBERS

1 Pump
2 Pump housing
3 Pumping mechanism
4 Pump inlet
5 Pump outlet
6 Programmable controller
7 Inlet tube
8 Outlet tube
9 Nozzle pipe
10 Nozzle pipe orifice
11 Container
12 Microemulsion to be tested
13 Pending drop
14 Detached (atomized) drops
15 Ruler with graduations that identify linear measures
L Length of the nozzle pipe
D Inner diameter of the nozzle pipe
H Height of the pending drop

The invention claimed is:
1. A cosmetic water-in-oil microemulsion comprising:
i) 20-40% w/w of oil phase ingredient(s) with spreadability value above 1700 mm$^2$/10 min at 25° C.,
ii) 15-35% w/w of oil phase ingredient(s) with spreadability value between 1000 and 1700 mm$^2$/10 min at 25° C.,
iii) 1-15% w/w of oil phase ingredient(s) with spreadability value between 500 and 999 mm$^2$/10 min at 25° C.,
iv) 0-10% w/w of oil phase ingredient(s) with spreadability value below 500 mm$^2$/10 min at 25° C.,
v) 0.2-15% w/w of co-surfactant(s) selected from glycerin, propylene glycol, 1,10-decanediol, 1,2-butanediol, 1,3-butanediol, 1,2-hexanediol, 1,4-butanediol, 1,5-pentanediol, 2,3-butanediol, hexanediol, ethyl hexanediol, isopentyldiol, methylpropanediol, propanediol, butylene glycol, dipropylene glycol, glycol, hexylene glycol, neopentyl glycol, pentylene glycol, 1,2,6-hexanetriol, mannitol, erythritol, xylitol or sorbitol,
vi) 0-10% w/w of co-solvent(s) selected from ethanol, 1-propanol or 2-propanol,
vii) 5-30% w/w of fatty acid ester(s) of glycerol or fatty acid ester(s) of polyglycerol,
viii) 5-20% w/w of water,
whereby the cosmetic water-in-oil microemulsion is dispensable at a constant flow rate of 0.05 ml/sec from a nozzle pipe orifice of a vertically positioned nozzle pipe with a length L of 15 mm and an inner diameter D of 2 mm and the height H of any of the pending drops that hang on the nozzle pipe orifice does not exceed 10 mm for at least 180 consecutive seconds at ambient conditions,
and whereby the spreadability value of the oil phase ingredient(s) (i)-(iv) is determined by a.) dispensing 20 microliters of the ingredient into the middle of filter paper disc with the following characteristics: grade 589/5, material cellulose, retention range 2-4 pm, thickness 0.17 mm, filtration time to Herzberg 450 s, weight 85 g/m$^2$, diameter 125 mm b.) measuring the area of filter paper wetted by the ingredient 10 minutes after dispensing and c.) expressing the spreadability value as wetted area in mm$^2$/10 min.

2. A cosmetic water-in-oil microemulsion as recited in claim 1, wherein the ingredients i) through viii) add up to a total of at least 95% w/w relative to the total weight of the microemulsion.

3. A cosmetic water-in-oil microemulsion as recited in claim 1, wherein the oil phase ingredient(s) with spreadability value above 1700 mm$^2$/10 min at 25° C. are selected from undecane, dodecane, tridecane, tetradecane, isohexadecane, propylheptyl caprylate and hydrogenated polyisobutene.

4. A cosmetic water-in-oil microemulsion as recited in claim 1, wherein the oil phase ingredient(s) with spreadability value between 1000 and 1700 mm$^2$/10 min at 25° C. are selected from hexyl laurate, dibutyl adipate, coco-caprylate, dicaprylyl carbonate, dicaprylyl ether, caprylyl caprylate/caprate, isopropyl myristate, isopropyl palmitate and isoamyl laurate.

5. A cosmetic water-in-oil microemulsion as recited in claim 1, wherein the oil phase ingredient(s) with spreadability value between 500 and 999 mm$^2$/10 min at 25° C. are selected from ethylhexyl palmitate, ethylhexyl stearate, coco-caprylate/caprate, diethylhexylcyclohexane, cetearyl isononanoate, decyl oleate, octyldodecanol, hexyldecanol, cetearyl ethylhexanoate, caprylic/capric triglyceride, coco-glycerides and propylene glycol dicaprylate/dicaprate.

6. A cosmetic water-in-oil microemulsion as recited in claim 1, wherein the oil phase ingredient(s) with spreadability value below 500 mm$^2$/10 min at 25° C. are selected from *Elaeis guineensis* oil, *Passiflora incarnata* seed oil, olus oil, C12-15 Alkyl Benzoate, polyoxypropylene 15 stearyl ether, 13-docosenoic acid, 9-octadecenyl ester, hexyldecyl stearate and triisostearin.

7. A cosmetic water-in-oil microemulsion as recited in claim 1, wherein the oil phase ingredient(s) with spreadability value below 500 mm$^2$/10 min at 25° C. are oils of plant origin or waxes of plant origin.

8. A cosmetic water-in-oil microemulsion as recited in claim 1, wherein the fatty acid ester(s) of glycerol or fatty acid ester(s) of polyglycerol are selected from monoglyceryl monoesters, monoglyceryl diesters, monoglyceryl triesters, polyglyceryl monoesters, polyglyceryl diesters or polyglyceryl multiesters.

9. A cosmetic water-in-oil microemulsion as recited in claim 1, wherein the water-in-oil microemulsion comprises at least two different fatty acid ester(s) of glycerol and/or fatty acid ester(s) of polyglycerol.

10. A cosmetic water-in-oil microemulsion as recited in claim 1, wherein the fatty acid ester(s) of glycerol or fatty acid ester(s) of polyglycerol are selected from polyglyceryl monoesters, polyglyceryl diesters or polyglyceryl multiesters with 5 repeating glycerol moieties.

11. A cosmetic water-in-oil microemulsion as recited in claim 1, wherein the water-in-oil microemulsion comprises water in the amounts between 6% w/w and 15% w/w.

12. A cosmetic water-in-oil microemulsion as recited in claim 1, wherein the ratio between the amount of water as weight % relative to the total weight of microemulsion and the amount of the emulsifier as weight % relative to the total weight of microemulsion ranges from 4:1 to 2:3.

13. A cosmetic water-in-oil microemulsion as recited in claim 1, wherein the water-in-oil microemulsion comprises at least one water-soluble extract of plant material.

14. A cosmetic water-in-oil microemulsion as recited in claim 1, wherein the water-in-oil microemulsion comprises at least one of emollients, occlusives, moisturizers, humectants, lipid layer enhancers, cosmetic auxiliary ingredients or cosmetic active ingredients.

15. A method of dispensing the cosmetic water-in-oil microemulsion according to claim 1, comprising dispensing the cosmetic water-in-oil microemulsion through a nozzle at volumetric flux from 0.01 ml per second per mm$^2$ to 25 ml per second per mm$^2$.

16. A cosmetic water-in-oil microemulsion as recited in claim 2, wherein the oil phase ingredient(s) with spreadability value above 1700 mm$^2$/10 min at 25° C. are selected from undecane, dodecane, tridecane, tetradecane, isohexadecane, propylheptyl caprylate and hydrogenated polyisobutene.

17. A cosmetic water-in-oil microemulsion as recited in claim 2, wherein the oil phase ingredient(s) with spreadability value between 1000 and 1700 mm$^2$/10 min at 25° C. are selected from hexyl laurate, dibutyl adipate, coco-caprylate, dicaprylyl carbonate, dicaprylyl ether, caprylyl caprylate/caprate, isopropyl myristate, isopropyl palmitate and isoamyl laurate.

18. A cosmetic water-in-oil microemulsion as recited in claim 3, wherein the oil phase ingredient(s) with spreadability value between 1000 and 1700 mm$^2$/10 min at 25° C. are selected from hexyl laurate, dibutyl adipate, coco-caprylate, dicaprylyl carbonate, dicaprylyl ether, caprylyl caprylate/caprate, isopropyl myristate, isopropyl palmitate and isoamyl laurate.

19. A cosmetic water-in-oil microemulsion as recited in claim 2, wherein the oil phase ingredient(s) with spreadability value between 500 and 999 mm$^2$/10 min at 25° C. are selected from ethylhexyl palmitate, ethylhexyl stearate, coco-caprylate/caprate, diethylhexylcyclohexane, cetearyl isononanoate, decyl oleate, octyldodecanol, hexyldecanol, cetearyl ethylhexanoate, caprylic/capric triglyceride, coco-glycerides and propylene glycol dicaprylate/dicaprate.

20. A cosmetic water-in-oil microemulsion as recited in claim 3, wherein the oil phase ingredient(s) with spreadability value between 500 and 999 mm$^2$/10 min at 25° C. are selected from ethylhexyl palmitate, ethylhexyl stearate, coco-caprylate/caprate, diethylhexylcyclohexane, cetearyl isononanoate, decyl oleate, octyldodecanol, hexyldecanol, cetearyl ethylhexanoate, caprylic/capric triglyceride, coco-glycerides and propylene glycol dicaprylate/dicaprate.

\* \* \* \* \*